US011717343B2

(12) United States Patent
Coates et al.

(10) Patent No.: US 11,717,343 B2
(45) Date of Patent: Aug. 8, 2023

(54) SYSTEMS, DEVICES, AND ASSOCIATED METHODS FOR NEUROMODULATION IN HETEROGENEOUS TISSUE ENVIRONMENTS

(71) Applicant: Medtronic Ireland Manufacturing Unlimited Company, Dublin (IE)

(72) Inventors: Paul J. Coates, Corte Madera, CA (US); Robert J. Melder, Santa Rosa, CA (US)

(73) Assignee: Medtronic Ireland Manufacturing Unlimited Company, Dublin (IE)

( * ) Notice: Subject to any disclaimer, the term of this patent is extended or adjusted under 35 U.S.C. 154(b) by 750 days.

(21) Appl. No.: 15/965,687

(22) Filed: Apr. 27, 2018

(65) Prior Publication Data

US 2019/0223945 A1 Jul. 25, 2019

Related U.S. Application Data

(60) Provisional application No. 62/621,351, filed on Jan. 24, 2018, provisional application No. 62/621,335, filed on Jan. 24, 2018.

(51) Int. Cl.
*A61B 18/14* (2006.01)
*A61B 18/12* (2006.01)
(Continued)

(52) U.S. Cl.
CPC ...... *A61B 18/1492* (2013.01); *A61B 18/1206* (2013.01); *A61N 1/0551* (2013.01);
(Continued)

(58) Field of Classification Search
CPC .......... A61B 18/1492; A61B 2018/124; A61B 2018/0016; A61B 18/16;
(Continued)

(56) References Cited

U.S. PATENT DOCUMENTS 7,653,438 B2  1/2010  Deem et al.
8,347,891 B2  1/2013  Demarais et al.
(Continued)

FOREIGN PATENT DOCUMENTS

EP  2457615  12/2014
EP  2918239  9/2015
(Continued)

OTHER PUBLICATIONS

International Searching Authority, International Search Report and Written Opinion for International Application No. PCT/US2019/014679, dated Apr. 17, 2019, 15 pages.
(Continued)

*Primary Examiner* — Michael F Peffley
*Assistant Examiner* — Yasamin Ekrami
(74) *Attorney, Agent, or Firm* — Shumaker & Sieffert, P.A.

(57) ABSTRACT

Systems and methods for neuromodulation therapy are disclosed herein. A method in accordance with embodiments of the present technology can include, for example, intravascularly positioning a plurality of ablation electrodes within a blood vessel lumen at a treatment site. The method can include analyzing a renal neuromodulation target site of a patient to obtain patient-specific data related to the renal neuromodulation target site, and based on the patient specific data, delivering neuromodulation treatment to the patient via one or more of the ablation electrodes.

22 Claims, 21 Drawing Sheets

(51) Int. Cl.
  *A61N 1/36* (2006.01)
  *A61N 1/05* (2006.01)
  *A61B 18/00* (2006.01)
  *A61B 18/16* (2006.01)
  *A61B 18/08* (2006.01)

(52) U.S. Cl.
  CPC ..... *A61N 1/36017* (2013.01); *A61N 1/36031* (2017.08); *A61N 1/36103* (2013.01); *A61N 1/36135* (2013.01); *A61B 18/082* (2013.01); *A61B 18/16* (2013.01); *A61B 2018/0016* (2013.01); *A61B 2018/00345* (2013.01); *A61B 2018/00434* (2013.01); *A61B 2018/00505* (2013.01); *A61B 2018/00511* (2013.01); *A61B 2018/00577* (2013.01); *A61B 2018/00714* (2013.01); *A61B 2018/00726* (2013.01); *A61B 2018/00791* (2013.01); *A61B 2018/00863* (2013.01); *A61B 2018/00875* (2013.01); *A61B 2018/00994* (2013.01); *A61B 2018/124* (2013.01); *A61B 2018/126* (2013.01); *A61B 2018/1253* (2013.01); *A61B 2018/1407* (2013.01); *A61B 2018/1435* (2013.01); *A61B 2018/1467* (2013.01); *A61B 2218/002* (2013.01); *A61N 1/0558* (2013.01)

(58) Field of Classification Search
  CPC ........ A61B 2018/00345; A61B 18/082; A61B 2018/1435; A61B 2018/00994; A61B 2018/00714; A61B 2018/00434; A61B 2018/1253; A61B 2018/126; A61B 2018/00863; A61B 2018/00577; A61B 2018/00511; A61B 2018/00875; A61B 2018/1467
  See application file for complete search history.

(56) References Cited

U.S. PATENT DOCUMENTS

| | | | |
|---|---|---|---|
| 8,888,773 B2 | 11/2014 | Chang et al. | |
| 9,084,610 B2 | 7/2015 | Goshgarian et al. | |
| 9,168,094 B2 | 10/2015 | Lee et al. | |
| 2004/0210214 A1 | 10/2004 | Knowlton | |
| 2005/0288730 A1 | 12/2005 | Deem et al. | |
| 2006/0004301 A1 | 1/2006 | Kasevich | |
| 2006/0235474 A1* | 10/2006 | Demarais | A61N 1/0551 607/2 |
| 2007/0088413 A1 | 4/2007 | Weber et al. | |
| 2007/0129720 A1 | 6/2007 | Demarais et al. | |
| 2008/0234671 A1* | 9/2008 | Marion | A61B 18/1233 606/41 |
| 2010/0010480 A1 | 1/2010 | Mehta et al. | |
| 2010/0145329 A1* | 6/2010 | Bystryak | A61B 18/00 606/33 |
| 2012/0116382 A1 | 5/2012 | Ku et al. | |
| 2012/0130359 A1* | 5/2012 | Turovskiy | A61B 18/02 606/21 |
| 2013/0012867 A1 | 1/2013 | Demarais et al. | |
| 2013/0096549 A1* | 4/2013 | Organ | A61B 18/14 606/33 |
| 2013/0197357 A1 | 8/2013 | Green et al. | |
| 2014/0316402 A1* | 10/2014 | Shah | A61B 18/1206 606/34 |
| 2014/0358140 A1 | 12/2014 | Emmons et al. | |
| 2014/0378966 A1 | 12/2014 | Haverkost et al. | |
| 2015/0112234 A1* | 4/2015 | McCaffrey | A61N 7/022 601/3 |
| 2015/0182740 A1* | 7/2015 | Mickelsen | A61M 25/0606 604/506 |
| 2015/0196357 A1* | 7/2015 | Chen | A61B 18/1206 606/41 |
| 2015/0245867 A1* | 9/2015 | Gross | A61B 18/1492 606/34 |
| 2016/0008067 A1* | 1/2016 | Hadjicostis | A61B 8/0891 600/439 |
| 2016/0095534 A1* | 4/2016 | Thakur | A61B 5/4842 600/547 |
| 2016/0095535 A1* | 4/2016 | Hettrick | A61B 18/1492 600/381 |
| 2017/0035402 A1* | 2/2017 | Matsui | H02J 50/12 |
| 2017/0333125 A1 | 11/2017 | Lepak et al. | |
| 2019/0069949 A1 | 3/2019 | Vrba et al. | |
| 2019/0223946 A1 | 7/2019 | Coates et al. | |

FOREIGN PATENT DOCUMENTS

| | | |
|---|---|---|
| EP | 2934357 | 11/2017 |
| WO | WO2007146834 | 12/2007 |
| WO | WO2012061153 | 5/2012 |
| WO | WO2012061161 | 5/2012 |
| WO | WO2013086461 | 6/2013 |
| WO | WO2014145164 | 9/2014 |
| WO | WO2014205388 | 12/2014 |
| WO | WO2015031643 | 3/2015 |
| WO | WO2015031648 | 3/2015 |
| WO | WO2015113027 | 7/2015 |
| WO | WO2015143372 | 9/2015 |
| WO | WO2015200518 | 12/2015 |
| WO | WO2017012907 | 1/2017 |

OTHER PUBLICATIONS

International Searching Authority, International Search Report and Written Opinion for International Application No. PCT/US2019/014684, dated Apr. 24, 2019, 15 pages.

Brown, "Electrical impedance tomography (EIT): a review," Journal of Medical Engineering and Technology, vol. 27, No. 3, May/Jun. 2003, pp. 107-108.

Esler et al., "Renal Denervation: Not as Easy as it Looks," Science Translational Medicine, vol. 7, No. 285, Apr. 29, 2015, 4 pages.

Mahfoud et al., "Efficacy and Safety of Catheter-Based Radiofrequency Renal Denervation in Stented Renal Arteries," Circ Cardiovasc Interv. 2014; 7 :813-818.

Wolf et al., "Noninvasive assessment of lung volume: Respiratory inductance plethysmography and electrical impedance tomography." Crit Care Med 2005; vol. 33(3) Supplement.S163-S169.

Coulombe et al., "A Parametric Model of the Relationship Between EIT and Total Lung Volume." Physiol Meas 2005;26(4):401-411.

Zhang et al., "EIT Images of Ventilation: What Contributes to the Resistivity Changes?" Physiol. Meas., 2005, 26(2): S81-S92.

Brown, "Electrical impedance tomography (EIT): a review," Journal of Medical Engineering & Technology. 2003; 27:97-108.

U.S. Provisional U.S. Appl. No. 62/588,215, by Doug Hettrick et al, filed Nov. 17, 2017.

U.S. Appl. No. 15/965,687, by Coates et al., filed Apr. 27, 2018.
U.S. Appl. No. 15/965,692, by Coates et al., filed Apr. 27, 2018.
U.S. Appl. No. 15/965,675, by Coates et al., filed Apr. 27, 2018.

Mark R. de Jong et al. "Renal Nerve Stimulation-Induced Blood Pressure Changes Predict Ambulatory Blood Pressure Response After Renal Denervation" Mar. 9, 2016, Hypertension 2016; 68:707-714.

International Preliminary Report on Patentability from International Application No. PCT/US2019/014679, dated Jul. 28, 2020, 9 pp.

\* cited by examiner

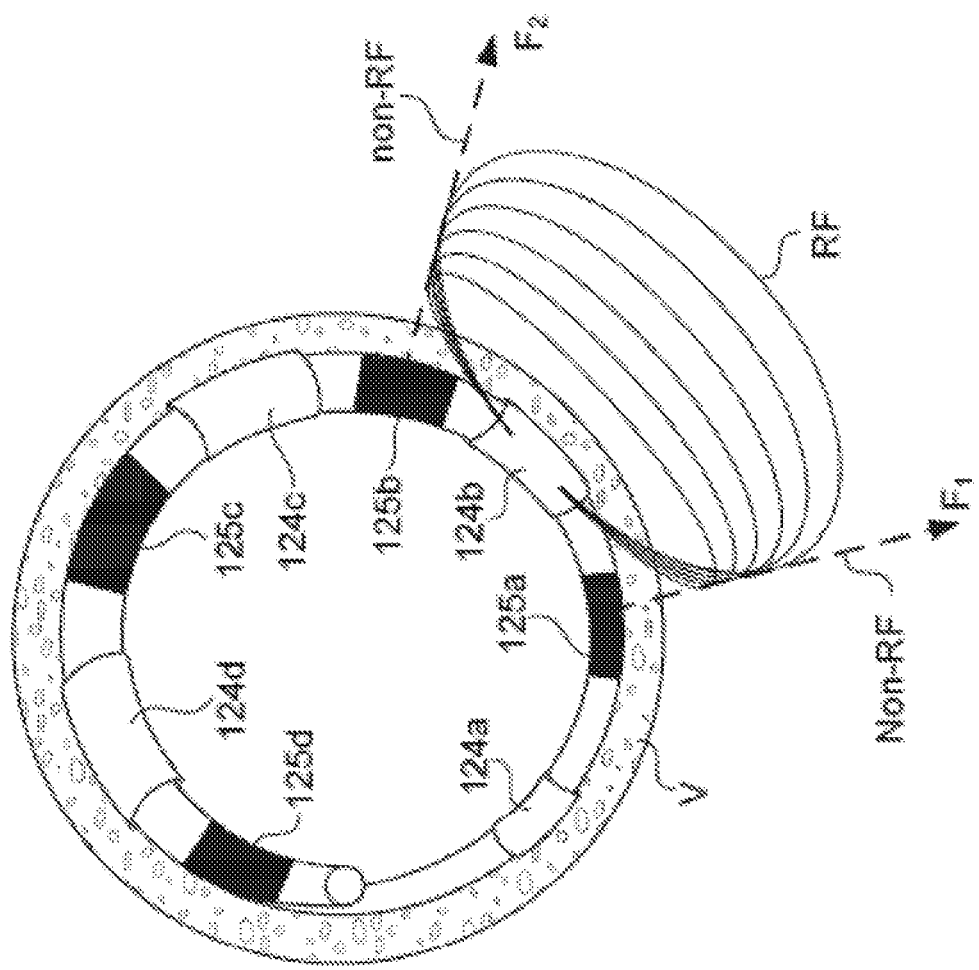
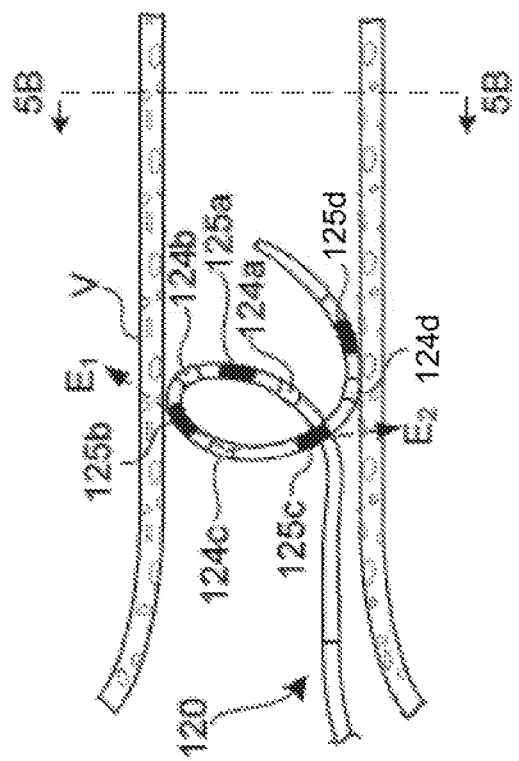
FIG. 5B
FIG. 5A

SYSTEMS, DEVICES, AND ASSOCIATED METHODS FOR NEUROMODULATION IN HETEROGENEOUS TISSUE ENVIRONMENTS

This application claims the benefit of U.S. Provisional Patent Application Ser. No. 62/621,351, filed on Jan. 24, 2018, and U.S. Provisional Patent Application Ser. No. 62/621,335, filed on Jan. 24, 2018, the entire content of each of which is incorporated by reference herein.

TECHNICAL FIELD

The present technology is related to neuromodulation. In particular, various embodiments of the present technology are related to systems and methods for renal neuromodulation in heterogeneous tissue environments.

BACKGROUND

The sympathetic nervous system (SNS) is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic over-activation of the SNS, however, is a common maladaptive response that can drive the progression of many disease states. Excessive activation of the renal SNS in particular has been identified experimentally and in humans as a likely contributor to the complex pathophysiology of arrhythmias, hypertension, states of volume overload (e.g., heart failure), and progressive renal disease.

Sympathetic nerves of the kidneys terminate in the renal blood vessels, the juxtaglomerular apparatus, and the renal tubules, among other structures. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone. For example, reduced renal blood flow and glomerular filtration rate as a result of renal sympathetic efferent stimulation is likely a cornerstone of the loss of renal function in cardio-renal syndrome, (i.e., renal dysfunction as a progressive complication of chronic heart failure). Pharmacologic strategies to thwart the consequences of renal sympathetic stimulation include centrally-acting sympatholytic drugs, beta blockers (e.g., to reduce renin release), angiotensin-converting enzyme inhibitors and receptor blockers (e.g., to block the action of angiotensin II and aldosterone activation consequent to renin release), and diuretics (e.g., to counter the renal sympathetic mediated sodium and water retention). These pharmacologic strategies, however, have significant limitations including limited efficacy, compliance issues, side effects, and others.

SUMMARY

The present technology is directed to devices, systems, and methods for neuromodulation, such as renal neuromodulation.

In some examples, the disclosure describes an example system including a catheter including an elongated member configured to be to be navigated through vasculature of a patient. The elongated member includes an electrode array. The electrode array includes a plurality of primary electrodes spaced apart along the elongated member, and a plurality of secondary electrodes spaced apart along the elongated member. The example system includes a medical device electrically coupled to the plurality of primary electrodes and the plurality of secondary electrodes. The medical device is configured to generate and deliver a radiofrequency (RF) energy field via at least one primary electrode of the plurality of primary electrodes. The RF energy field is configured to ablate nerves at or adjacent a target tissue site. The medical device is configured to generate and deliver a non-RF energy field via at least one secondary electrode of the plurality of secondary electrodes substantially simultaneously with the RF energy field. The non-RF energy field is configured to avoid ablating the nerves at or adjacent the target tissue site.

In some examples, the disclosure describes an example technique including controlling, by a processor, a medical device to generate and deliver a radiofrequency (RF) energy field via at least one primary electrode of a plurality of primary electrodes of an electrode array positioned on an elongated member of a catheter. The RF energy field is configured to ablate nerves at or adjacent a target tissue site. The electrode array includes the plurality of primary electrodes spaced apart along the elongated member, and a plurality of secondary electrodes spaced apart along the elongated member. The example technique includes controlling, by the processor, the medical device to generate and deliver a non-RF energy field via at least one secondary electrode of the plurality of secondary electrodes substantially simultaneously with the RF energy field. The non-RF energy field is configured to avoid ablating the nerves at or adjacent the target tissue site.

In some examples, the disclosure describes an example system including means for generating and delivering a radiofrequency (RF) energy field. The RF energy field is configured to ablate nerves at or adjacent a target tissue site. The example system includes means for generating and delivering a non-RF energy field substantially simultaneously with the RF energy field. The non-RF energy field is configured to avoid ablating the nerves at or adjacent the target tissue site.

Clause 1: A system, comprising: a catheter comprising an elongated member configured to be to be navigated through vasculature of a patient, wherein the elongated member comprises an electrode array, the electrode array including: a plurality of primary electrodes spaced apart along the elongated member, and a plurality of secondary electrodes spaced apart along the elongated member; and a medical device electrically coupled to the plurality of primary electrodes and the plurality of secondary electrodes, wherein the medical device is configured to: generate and deliver a radiofrequency (RF) energy field via at least one primary electrode of the plurality of primary electrodes, wherein the RF energy field is configured to ablate nerves at or adjacent a target tissue site, and generate and deliver a non-RF energy field via at least one secondary electrode of the plurality of secondary electrodes substantially simultaneously with the RF energy field, wherein the non-RF energy field is configured to avoid ablating the nerves at or adjacent the target tissue site.

Clause 2: The system of clause 1, wherein the non-RF energy field substantially inhibits the RF energy field from extending beyond the non-RF energy field.

Clause 3: The system of clause 1 or 2, wherein the non-RF energy field is configured to guide the RF energy field to the nerves at or adjacent the target tissue site.

Clause 4: The system of any of clauses 1 to 3, wherein the plurality of primary electrodes includes a coupled electrode pair including a first primary electrode and a second primary electrode proximate one another, and wherein the RF energy field includes a bipolar RF energy field delivered via the first primary electrode and the second primary electrode of the coupled electrode pair.

Clause 5: The system of clause 4, wherein the coupled electrode pair is a first coupled electrode pair, and wherein the plurality of primary electrodes includes a third primary electrode and a fourth primary electrode, wherein the plurality of primary electrodes includes a second coupled electrode pair including the second primary electrode and the third primary electrode, wherein the plurality of primary electrodes includes a third coupled electrode pair including the third primary electrode and the fourth primary electrode, wherein the bipolar RF energy field is a first bipolar RF energy field, and wherein the medical device is configured to generate and deliver the first bipolar RF energy field via the first coupled pair, a second bipolar RF field via the second coupled pair, and a third bipolar RF energy field via the third coupled pair.

Clause 6: The system of clause 4, wherein the plurality of secondary electrodes includes a first secondary electrode and a second secondary electrode spaced apart from the first secondary electrode, wherein the first primary electrode is positioned on the elongated member between the first and second secondary electrodes, wherein the non-RF energy field includes a first non-RF energy field, and wherein the medical device is configured to: generate and deliver the first non-RF energy field via the first secondary electrode; and generate and deliver a second non-RF energy field via the second secondary electrode, wherein one or both of the first or the second non-RF energy fields substantially inhibit the bipolar RF energy field from extending beyond the first or second non-RF energy fields.

Clause 7: The system of any of clauses 1 to 6, wherein at least one of the plurality of secondary electrodes differs in at least one electrode characteristic from at least one of the plurality of primary electrodes.

Clause 8: The system of any of clauses 1 to 7, wherein the elongated member further comprises a plurality of thermal elements spaced apart from one another, wherein the medical device is configured to deliver, via the thermal elements, non-ablative thermal energy, at or below about 45° C., to a target tissue site or areas adjacent the target tissue site.

Clause 9: The system of any of clauses 1 to 8, wherein tissue adjacent the target tissue site includes injected electrically conductive material or injected electrically insulative material, and wherein the injected electrically conductive material or injected electrically insulative material causes a substantially uniform local impedance field at or adjacent the target tissue site.

Clause 10: A method, comprising: controlling, by a processor, a medical device to generate and deliver a radiofrequency (RF) energy field via at least one primary electrode of a plurality of primary electrodes of an electrode array positioned on an elongated member of a catheter, wherein the RF energy field is configured to ablate nerves at or adjacent a target tissue site, wherein the electrode array includes: the plurality of primary electrodes spaced apart along the elongated member, and a plurality of secondary electrodes spaced apart along the elongated member; and controlling, by the processor, the medical device to generate and deliver a non-RF energy field via at least one secondary electrode of the plurality of secondary electrodes substantially simultaneously with the RF energy field, wherein the non-RF energy field is configured to avoid ablating the nerves at or adjacent the target tissue site.

Clause 11: The method of clause 10, wherein the non-RF energy field substantially inhibits the RF energy field from extending beyond the non-RF energy field.

Clause 12: The method of clause 10 or 11, wherein the non-RF energy field is configured to guide the RF energy field to the nerves at or adjacent the target tissue site.

Clause 13: The method of any of clauses 10 to 12, wherein the plurality of primary electrodes includes a coupled electrode pair including a first primary electrode and a second primary electrode proximate one another, and wherein the RF energy field includes a bipolar RF energy field delivered via the first primary electrode and the second primary electrode of the coupled electrode pair.

Clause 14: The method of clause 13, wherein the coupled electrode pair is a first coupled electrode pair, and wherein the plurality of primary electrodes includes a third primary electrode and a fourth primary electrode, wherein the plurality of primary electrodes includes a second coupled electrode pair including the second primary electrode and the third primary electrode, wherein the plurality of primary electrodes includes a third coupled electrode pair including the third primary electrode and the fourth primary electrode, wherein the bipolar RF energy field is a first bipolar RF energy field, and wherein the method comprises: controlling, by the processor, the medical device to deliver the first bipolar RF energy field via the first coupled pair; controlling, by the processor, the medical device to deliver the second bipolar RF energy field via the second coupled pair; and controlling, by the processor, the medical device to deliver the third bipolar RF energy field via the third coupled pair.

Clause 15: The method of clause 13 or 14, wherein the plurality of secondary electrodes includes a first secondary electrode and a second secondary electrode spaced apart from the first secondary electrode, wherein the first primary electrode is positioned on the elongated member between the first and second secondary electrodes, and wherein the method comprises: controlling, by the processor, the medical device to generate and deliver a first non-RF energy field via the first secondary electrode; and controlling, by the processor, the medical device to generate and deliver a second non-RF energy field via the second secondary electrode, wherein one or both of the first or the second non-RF energy fields substantially inhibit the bipolar RF energy field from extending beyond the first or second non-RF energy fields.

Clause 16: The method of any of clauses 10 to 15, wherein the elongated member further comprises a plurality of thermal elements spaced apart from one another, and wherein the method further comprises, controlling, by the processor, the medical device to deliver, via the thermal elements, non-ablative thermal energy, at or below about 45° C., to a target tissue site or areas adjacent the target tissue site.

Clause 17: The method of any of clauses 10 to 16, wherein tissue adjacent the target tissue site includes injected electrically conductive material or injected electrically insulative material, and wherein the injected electrically conductive material or injected electrically insulative material causes a substantially uniform local impedance field at or adjacent the target tissue site.

Clause 18: A system, comprising: means for generating and delivering a radiofrequency (RF) energy field, wherein the RF energy field is configured to ablate nerves at or adjacent a target tissue site; and means for generating and delivering a non-RF energy field substantially simultaneously with the RF energy field, wherein the non-RF energy field is configured to avoid ablating the nerves at or adjacent the target tissue site.

Clause 19: The system of clause 18, wherein the non-RF energy field substantially inhibits the RF energy field from extending beyond the non-RF energy field.

Clause 20: The system of clause 18 or 19, wherein the non-RF energy field is configured to guide the RF energy field to the nerves at or adjacent the target tissue site.

Clause 21: A method, comprising: analyzing a renal neuromodulation target site of a human patient to obtain patient-specific data related to the renal neuromodulation target site; based on the obtained patient-specific data, updating one or more parameters of an algorithm for delivering renal neuromodulation treatment via one or more energy delivery elements of a renal neuromodulation catheter; and at least partially ablating renal nerves of the patient at the renal neuromodulation target site via energy from one or more of the energy delivery elements, wherein the energy is delivered via the energy delivery elements according to the updated parameters of the algorithm.

Clause 22: The method of clause 21 wherein analyzing the renal neuromodulation target site includes performing at least one of imaging, modeling, and mapping the renal neuromodulation target site.

Clause 23: The method of clause 21 or 22 wherein analyzing the renal neuromodulation target site includes determining (a) distances between one or more of the ablation electrodes, or (b) impedance data of different combinations of the ablation electrodes.

Clause 24: The method of any of clauses 21 to 23 wherein the patient specific data relates to at least one of electrical properties, thermal properties, thickness and configuration of tissue at the renal neuromodulation target site.

Clause 25: The method of any of clauses 21 to 24 wherein analyzing the renal neuromodulation target site is performed while energy is being delivered to the patient via the energy delivery elements.

Clause 26: The method of any of clauses 21 to 25, further comprising iteratively repeating the operations of analyzing, updating and at least partially ablating the renal nerves via energy from the one or more energy delivery elements in a closed loop manner.

Clause 27: A system, comprising: a neuromodulation catheter including—an elongated shaft having a distal portion configured to be intravascularly positioned at a target site within a blood vessel of a human patient, and a plurality of primary electrodes spaced apart along the distal portion of the shaft, the plurality of primary electrodes including a first primary electrode and a second primary electrode, wherein the primary electrodes are configured to deliver neuromodulation energy to target nerves at or adjacent the target site; and a controller configured to be communicatively coupled to the primary electrodes, wherein the controller is further configured to provide an algorithm having parameters for delivering neuromodulation treatment via one or more of the primary electrodes.

Clause 28: The system of clause 27 wherein the first and second primary electrodes comprise a coupled electrode pair, and wherein the controller is configured to deliver a bipolar RF energy field to the target site via the coupled electrode pair.

Clause 29: The system of clause 27 or 28 wherein the first and second primary electrodes are non-adjacent electrodes such that a third primary electrode is positioned along the distal portion of the shaft between the first and second primary electrodes.

Clause 30: The system of any of clauses 27 to 29 wherein the first primary electrode is adjacent the second primary electrode, wherein the neuromodulation catheter comprises a third primary electrode adjacent the second primary electrode, and a fourth primary electrode adjacent the third primary electrode, wherein the first and second primary electrodes comprise a first coupled pair, the second and third primary electrodes comprise a second coupled pair, and the third and fourth primary electrodes comprise a third coupled pair, and wherein the controller is configured to sequentially deliver bipolar RF energy fields via the first coupled pair, the second coupled pair, and the third coupled pair.

Clause 31: The system of any of clauses 27 to 30 wherein the neuromodulation shaft further comprises a plurality of secondary electrodes spaced apart from one another along the distal portion of the shaft, wherein the primary electrodes are configured to deliver RF energy fields and the secondary electrodes are configured to deliver non-RF energy fields.

Clause 32. The system of clause 31 wherein the secondary electrodes include a first secondary electrode and a second secondary electrode spaced apart from the first secondary electrode, wherein the first primary electrode is positioned on the neuromodulation shaft between the first and second secondary electrodes, and wherein the controller is configured to: emit a first non-RF energy field from the first secondary electrode; emit a second non-RF energy field from the second secondary electrode; and emit an RF energy field from the first primary electrode, wherein the RF energy field is substantially inhibited from traveling beyond the first or second non-RF energy fields.

Clause 33. The system of clause 31 or 32 wherein one or more of the secondary electrodes serve as return electrodes for one or more of the primary electrodes.

Clause 34. The system of clause 33 wherein the neuromodulation shaft further comprises a plurality of thermal elements spaced apart from one another along the distal portion of the shaft, wherein the primary electrodes are configured to deliver RF energy fields and the thermal elements are configured to deliver non-ablative thermal energy, at or below about 45° C., to the target site or areas adjacent the target site.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

Reference is made to the attached drawings, wherein elements having the same reference numeral designations represent similar elements throughout and wherein:

FIG. 5A illustrates a partially schematic side view of a neuromodulation assembly, and FIG. 5B illustrates a partially schematic end view of the neuromodulation assembly, in accordance with some embodiments of the present technology.

DETAILED DESCRIPTION

Figure 1:
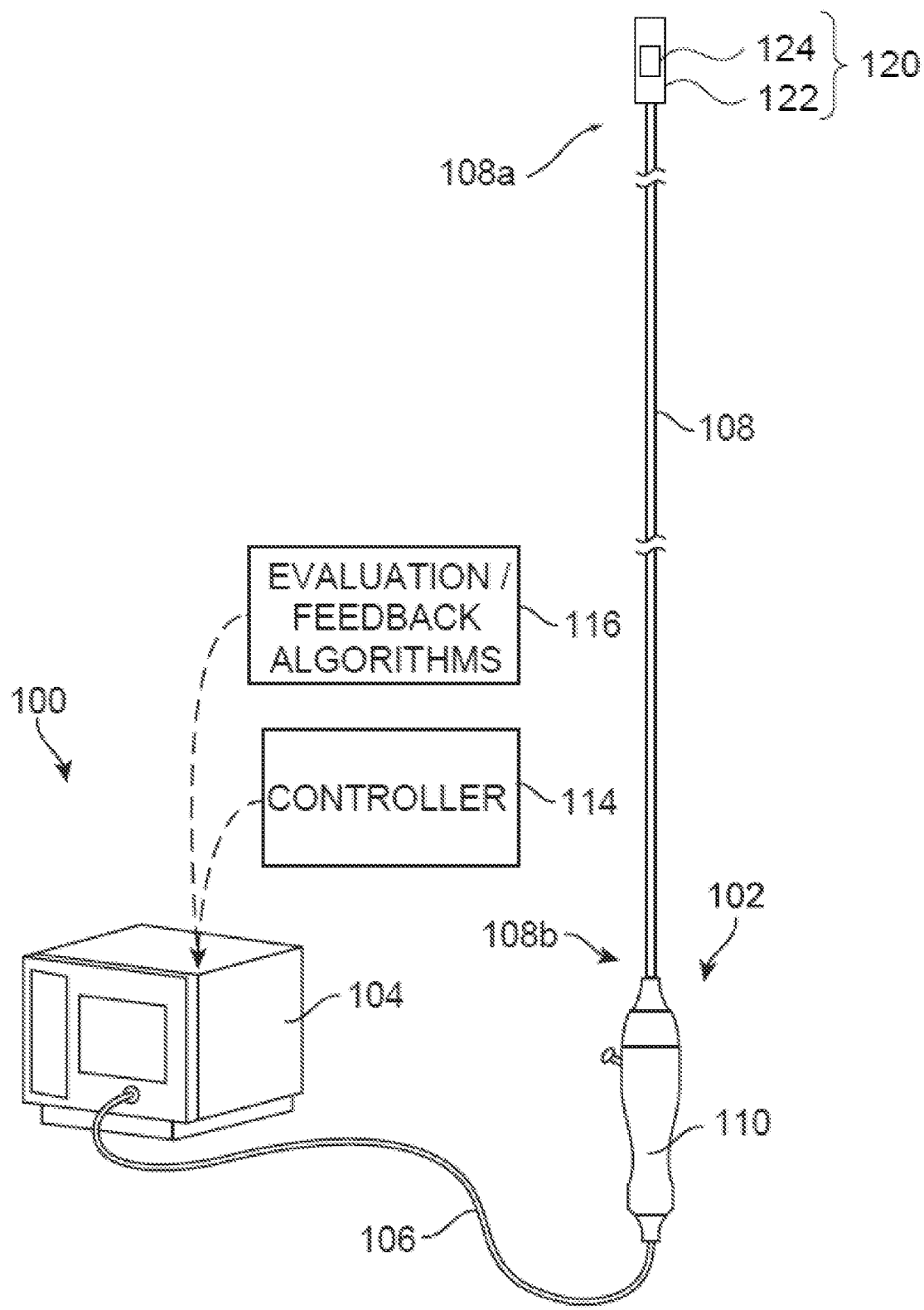
FIG. 1 is a partially schematic illustration of a neuromodulation system configured in accordance with some embodiments of the present technology.

The present technology is directed to devices, systems, and methods for neuromodulation, such as renal neuromodulation. In some embodiments, the present technology includes methods for selecting combinations of ablation electrodes for the purpose of influencing the size, shape, and directionality of the electrical fields emanating from the ablation electrodes during treatment. The spatial and directional properties of the ablative energy directly affect the three-dimensional shape of the lesion(s) (i.e., damaged tissue) created by the ablative energy, as well as the position of the lesion(s) relative to the artery or other blood vessel in which the ablation electrodes are positioned during treatment. Accordingly, the present technology leverages the spatial relationships between ablation electrodes (e.g., primary electrodes) and/or other features, such as reference electrodes, non-ablation electrodes (e.g., secondary electrodes) and thermal elements, to better concentrate the ablative energy on the targeted nerves, and improve efficacy of neuromodulation treatment while minimizing/inhibiting the delivery of ablative energy to non-target tissue. Furthermore, some embodiments of the present technology disclose performing pre-procedural analysis of an intravascular treatment site within the patient prior to delivering neuromodulation. The analysis can then be used to adjust or tailor the neuromodulation for that particular patient. As discussed in greater detail below, therapeutically-effective renal neuromodulation can include rendering neural fibers inert, inactive, or otherwise completely or partially reduced in function.

Specific details of several embodiments of the technology are described below with reference to FIGS. 1-7. The embodiments can include, for example, modulating nerves proximate (e.g., at or near) a renal artery, a renal vein, and/or other suitable structures. Although many of the embodiments are described herein with respect to electrically-induced approaches, other treatment modalities in addition to those described herein are within the scope of the present technology. Additionally, other embodiments of the present technology can have different configurations, components, or procedures than those described herein. A person of ordinary skill in the art, therefore, will accordingly understand that the technology can have other embodiments with additional elements, and that the technology can have other embodiments without several of the features shown and described below with reference to FIGS. 1-7.

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device.

Some conventional renal denervation devices employ a multi-electrode, unipolar electrode system that delivers radio frequency (RF) energy to the endovascular surface of the renal artery (or other blood vessels) for the purpose of ablating nerves at the extravascular surface of the artery (or other blood vessels). In some examples, an RF energy may be energy associated with a frequency in a range of greater than 20 (kilohertz) kHz, for example, more than about 20 kHz, or more than about 1 (megahertz) MHz, or more than about 100 MHz, or more than about 500 MHz, or more than about 1 (gigahertz) GHz, or more than about 100 GHz, or less than about 300 GHz. An example of one such system is the multi-electrode Symplicity Spyral™ catheter along with a Symplicity G3™ generator. The catheter and generator are commercially available from Medtronic, Inc. The shape of the electric field and relative penetration depth of current densities strong enough to damage nerve tissue depend on several factors including, among others, the power and duration of energy delivery, the geometric shape of the electrodes, the electrode material, and the apposition of the electrodes against the vessel wall. The shape and current density of the electric field within the tissue also depends on the relative conductive properties of the tissue through which the current travels based on the relative three-dimensional conductivity of each individual tissue.

FIG. 1 is a partially schematic illustration of a neuromodulation system 100 ("system 100") configured in accordance with some embodiments of the present technology. As shown in FIG. 1, the system 100 includes a neuromodulation catheter 102, a console 104, and a cable 106 extending therebetween. The neuromodulation catheter 102 can include an elongated shaft 108 having a proximal portion 108b, a distal portion 108a, a handle 110 operably connected to the shaft 108 at the proximal portion 108b, and a neuromodulation assembly 120 operably connected to the shaft 108 at the distal portion 108a. The shaft 108 and the neuromodulation assembly 120 can be 2, 3, 4, 5, 6, or 7 French or another suitable size. As shown schematically in FIG. 1, the neuromodulation assembly 120 (shown schematically) can include a support structure 122 carrying an array of two or more ablation electrodes 124 (also referred to as "primary electrodes") spaced apart along the shaft 108. The ablation electrodes 124 can be configured to apply electrical stimuli (e.g., RF energy) to target sites at or proximate to vessels within a patient, temporarily stun nerves, deliver neuromodulation energy to target sites, and/or detect vessel impedance. In some embodiments, the ablation electrodes 124 may be shaped to improve/enhance contact with the vessel wall. For example, the ablation electrodes 124 may be shaped such that an outer or engagement surface of the individual electrodes more closely matches the shape of the vessel wall to ensure maximum wall contact (and thereby enhance reliable energy delivery).

The distal portion 108a of the shaft 108 is configured to be moved within a lumen of a human patient and locate the neuromodulation assembly 120 at a target site within or otherwise proximate to the lumen. For example, the shaft 108 can be configured to position the neuromodulation assembly 120 within a blood vessel, a duct, an airway, or another naturally occurring lumen within the human body. In certain embodiments, intravascular delivery of the neuromodulation assembly 120 includes percutaneously inserting a guide wire (not shown) into a body lumen of a patient and moving the shaft 108 and/or the neuromodulation assembly 120 along the guide wire until the neuromodulation assembly 120 reaches a target site (e.g., a renal artery). For example, the distal end of the neuromodulation assembly 120 may define a passageway for engaging the guide wire for delivery of the neuromodulation assembly 120 using over-the-wire (OTW) or rapid exchange (RX) techniques. In other embodiments, the neuromodulation catheter 102 can be a steerable or non-steerable device configured for use without a guide wire. In still other embodiments, the neuromodulation catheter 102 can be configured for delivery via a guide catheter or sheath (not shown).

Once at the target site, the neuromodulation assembly 120 can be configured to apply stimuli, detect resultant hemodynamic responses, and provide or facilitate neuromodulation therapy at the target site (e.g., using the ablation electrodes 124 and/or other energy delivery elements). For example, the neuromodulation assembly 120 can detect vessel impedance via the ablation electrodes 124, blood flow via a flow sensing element (e.g., a Doppler velocity sensing element), local blood pressure within the vessel via a pressure transducer or other pressure sensing element, and/or other hemodynamic parameters. In some embodiments, the neuromodulation assembly 120 can detect vessel impedance via sensing elements separate from the ablation electrodes 124. In such embodiments, the neuromodulation assembly 120 may detect impedance with one or both of the sensing elements and the ablation electrodes 124. The detected responses can be transmitted to the console 104 and/or another device external to the patient. The console 104 can be configured to receive and store the recorded impedance or other measurements for further use by a clinician or operator. For example, a clinician can use the impedance measurements received by the console 104 to select combinations of ablation electrodes and reference electrodes, as described in greater detail below.

The console 104 can be configured to control, monitor, supply, and/or otherwise support operation of the neuromodulation catheter 102. The console 104 can further be configured to generate a selected form and/or magnitude of energy for delivery to tissue at the target site via the neuromodulation assembly 120, and therefore the console 104 may have different configurations depending on the treatment modality of the neuromodulation catheter 102. For example, the console 104 can include an energy generator (not shown) configured to generate RF energy. In some embodiments, the system 100 may be configured to deliver a monopolar electric field via one or more of the ablation electrodes 124 and one or more reference electrodes (not shown). The reference electrodes may be electrically connected to the console 104 and positioned on the neuromodulation assembly or at the skin of the patient at multiple locations to help direct and shape the electric field generated by the ablation electrodes 124 (as discussed in greater detail below with reference to FIGS. 3, 5A and 5B). In embodiments including multiple ablation electrodes 124, the ablation electrodes 124 may deliver power independently (i.e., may be used in a monopolar fashion), either simultaneously, selectively, or sequentially, and/or may deliver power between any desired combination of the ablation electrodes 124 (i.e., may be used in a bipolar fashion). In addition, an operator optionally may be permitted to choose which ablation electrodes 124 are used for power delivery in order to form highly customized lesion(s) within the renal artery, as desired. One or more sensing elements (not shown), such as one or more temperature (e.g., thermocouple, thermistor, etc.), pressure, optical, flow, chemical, and/or other sensing elements, may be located proximate to, within, or integral with the ablation electrodes 124. The sensing element(s) and the ablation electrodes 124 can be connected to one or more supply wires (not shown) that transmit signals from the sensing element(s) and/or convey energy to the ablation electrodes 124.

In various embodiments, the system 100 can further include a controller 114 communicatively coupled to the neuromodulation catheter 102. The controller 114 can be configured to initiate, terminate, and/or adjust operation of one or more components (e.g., the ablation electrodes 124) of the neuromodulation catheter 102 directly and/or via the console 104. For example, as described in greater detail below, the controller 114 may be configured to continuously or intermittently monitor the impedance between each of the ablation electrodes 124 and each of the reference electrodes (not shown) and, based on those measurements, select particular ablation electrode 124/reference electrode groupings that provide optimal electric fields for efficacious neuromodulation therapy.

In some examples, the reference electrode(s) tend to be at a relatively far distance from ablation electrodes 124. Electrical fields that are generated by ablation electrodes 124, with return path through a reference electrode, are referred to as a monopolar energy fields. Controller 114 may be configured to determine bipolar electrical fields for efficacious neuromodulation therapy. Bipolar electrical fields are generated by one of ablation electrodes 124, with return path through another one of ablation electrodes, that are located proximately to one another. As described in more detail, in one or more examples, controller 114 may determine monopolar and bipolar electrical fields based on various factors such as the needed volume of influence.

Furthermore, controller 114 may be configured to multiple different types of fields. For example, the electrical field generated via ablation electrodes 124 may have ablative effects. However, to control the volume of influence of the electrical field, controller 114 may determine a guiding electrical field that shapes the electrical field used for ablative effect but the guiding electrical field may not provide any ablative effect. As described in more detail, the electrical field used for ablative effects is referred to as a radio frequency (RF) energy field, and the guiding electrical field for shaping the RF energy field is referred to as a non-RF energy field. The RF energy field may be generated by ablation electrodes (e.g., primary electrodes) 124, and the non-RF energy field may be generated by secondary electrodes.

In some embodiments, the controller 114 can be a component separated from the console 104, such as within the handle 110, along the cable 106, etc. The controller 114 can be configured to execute one or more automated control algorithms and/or to receive control instructions from an operator. Further, the console 104 can be configured to provide feedback to an operator before, during, and/or after a treatment procedure via an evaluation/feedback algorithm 116 (e.g., such as changing ablation electrode 124/reference electrode groupings in response to impedance measurements).

Figure 2:
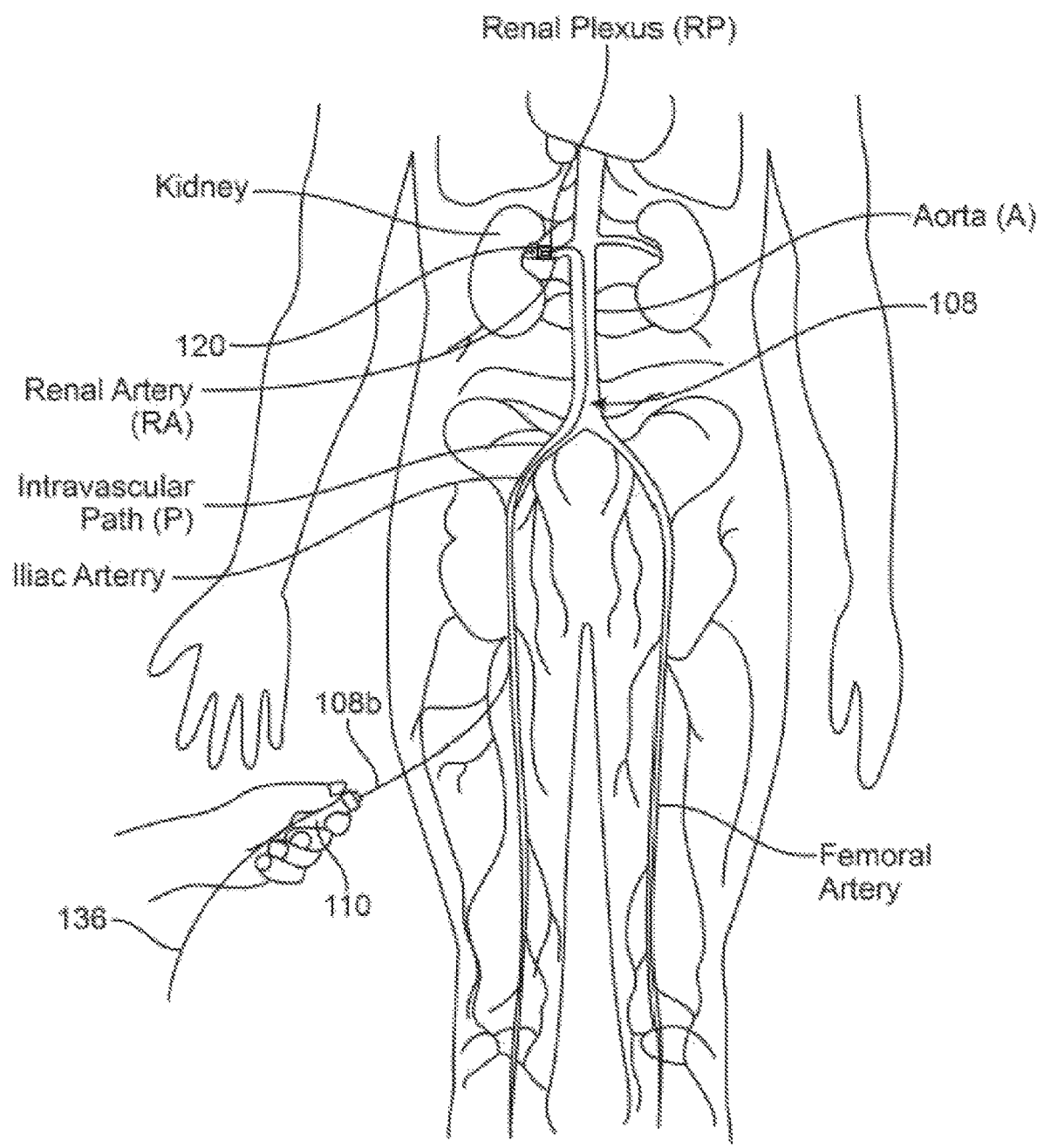
FIGS. 2 and 3 illustrate modulating renal nerves with the system of FIG. 1 in accordance with some embodiments of the present technology.

FIG. 2 (with additional reference to FIG. 1) illustrates gaining access to renal nerves in accordance with some embodiments of the present technology. The neuromodulation catheter 102 provides access to the renal plexus RP through an intravascular path P, such as a percutaneous access site in the femoral (illustrated), brachial, radial, or axillary artery to a targeted treatment site within a respective renal artery RA. By manipulating the proximal portion 108b of the shaft 108 from outside the intravascular path P, a clinician may advance the shaft 108 through the sometimes tortuous intravascular path P and remotely manipulate the distal portion 108a (FIG. 1) of the shaft 108. In the embodiment illustrated in FIG. 2, the neuromodulation assembly 120 is delivered intravascularly to the treatment site using a guide wire 136 in an OTW technique. As noted previously, the distal end of the neuromodulation assembly 120 may define a passageway for receiving the guide wire 136 for delivery of the neuromodulation catheter 102 using either OTW or RX techniques. At the treatment site, the guide wire 136 can be at least partially withdrawn or removed, and the neuromodulation assembly 120 can transform or otherwise be moved to a deployed arrangement for recording neural activity and/or delivering energy at the treatment site. In other embodiments, the neuromodulation assembly 120 may be delivered to the treatment site within a guide sheath (not shown) with or without using the guide wire 136. When the neuromodulation assembly 120 is at the target site, the guide sheath may be at least partially withdrawn or retracted and the neuromodulation assembly 120 can be transformed into the deployed arrangement. In still other embodiments, the shaft 108 may be steerable itself such that the neuromodulation assembly 120 may be delivered to the treatment site without the aid of the guide wire 136 and/or guide sheath.

Image guidance, e.g., computed tomography (CT), fluoroscopy, intravascular ultrasound (IVUS), optical coherence tomography (OCT), intracardiac echocardiography (ICE), or another suitable guidance modality, or combinations thereof, may be used to aid the clinician's positioning and manipulation of the neuromodulation assembly 120. For example, a fluoroscopy system (e.g., including a flat-panel detector, x-ray, or c-arm) can be rotated to accurately visualize and identify the target treatment site. In other embodiments, the treatment site can be determined using IVUS, OCT, and/or other suitable image mapping modalities that can correlate the target treatment site with an identifiable anatomical structure (e.g., a spinal feature) and/or a radiopaque ruler (e.g., positioned under or on the patient) before delivering the neuromodulation assembly 120. Further, in some embodiments, image guidance components (e.g., IVUS, OCT) may be integrated with the neuromodulation catheter 102 and/or run in parallel with the neuromodulation catheter 102 to provide image guidance during positioning of the neuromodulation assembly 120. For example, image guidance components (e.g., IVUS or OCT) can be coupled to the neuromodulation assembly 120 to provide three-dimensional images of the vasculature proximate the target site to facilitate positioning or deploying the multi-electrode assembly within the target renal blood vessel.

Renal neuromodulation is the partial or complete incapacitation or other effective disruption of nerves of the kidneys (e.g., nerves terminating in the kidneys or in structures closely associated with the kidneys). In particular, renal neuromodulation can include inhibiting, reducing, and/or blocking neural communication along neural fibers (e.g., efferent and/or afferent neural fibers) of the kidneys. Such incapacitation can be long-term (e.g., permanent or for periods of months, years, or decades) or short-term (e.g., for periods of minutes, hours, days, or weeks). Renal neuromodulation is expected to contribute to the systemic reduction of sympathetic tone or drive and/or to benefit at least some specific organs and/or other bodily structures innervated by sympathetic nerves. Accordingly, renal neuromodulation is expected to be useful in treating clinical conditions associated with systemic sympathetic overactivity or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions.

Renal neuromodulation can be electrically-induced, thermally-induced, chemically-induced, or induced in another suitable manner or combination of manners at one or more suitable target sites during a treatment procedure. The target site can be within or otherwise proximate to a renal lumen (e.g., a renal artery, a ureter, a renal pelvis, a major renal calyx, a minor renal calyx, or another suitable structure), and the treated tissue can include tissue at least proximate to a wall of the renal lumen. For example, with regard to a renal artery, a treatment procedure can include modulating nerves in the renal plexus, which lay intimately within or adjacent to the adventitia of the renal artery.

Renal neuromodulation can include an electrode-based or transducer-based treatment modality alone or in combination with another treatment modality. As discussed herein, for example, electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic renal nerve can slow or potentially block conduction of neural signals to produce a prolonged or permanent reduction in renal sympathetic activity. A variety of suitable types of energy can be used to stimulate and/or heat tissue at a treatment location. For example, neuromodulation in accordance with embodiments of the present technology can include delivering RF energy, pulsed electrical energy, or another suitable type of energy in combination with the electrical energy. An electrode or transducer used to deliver this energy can be used alone or with other electrodes or transducers in a multi-electrode or multi-transducer array. Furthermore, the energy can be applied from within the body (e.g., within the vasculature or other body lumens in a catheter-based approach) and/or from outside the body (e.g., via an applicator positioned outside the body). Furthermore, energy can be used to reduce damage to non-targeted tissue when targeted tissue adjacent to the non-targeted tissue is subjected to neuromodulating cooling.

In certain embodiments, neuromodulation may utilize one or more devices including, for example, catheter devices such as the Symplicity Spyral™ catheter mentioned previously (Medtronic, Inc.). Other suitable thermal devices are described in U.S. Pat. Nos. 7,653,438, 8,347,891, and 9,084,610. Other suitable devices and technologies are described in International Patent Application No. PCT/US2015/021835, filed Mar. 20, 2015, and International Patent Application No. PCT/US2015/013029, filed Jan. 27, 2015. Further, electrodes (or other energy delivery elements) can be used alone or with other electrodes in a multi-electrode array. Examples of suitable multi-electrode devices are described in U.S. patent application Ser. No. 13/281,360, filed Oct. 25, 2011, and U.S. Pat. No. 8,888,773. All of the foregoing patent references are incorporated herein by reference in their entireties.

Figure 3:
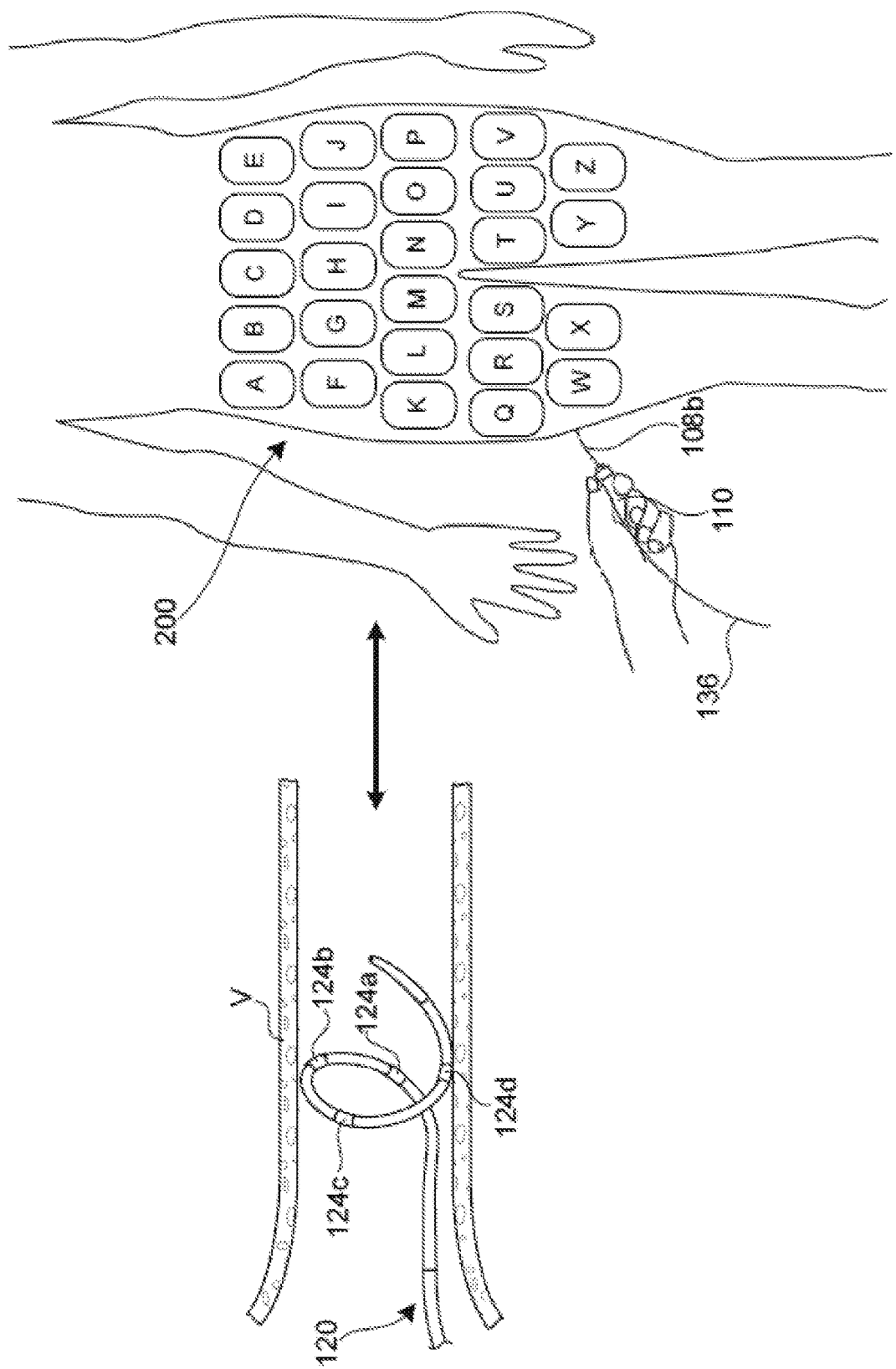

FIG. 3 illustrates another view of gaining access to renal nerves in accordance with some embodiments of the present technology. As shown schematically in FIG. 3, a plurality of reference electrodes 200 (individually labeled A-Z) may be positioned about the patient's abdominal area while the neuromodulation assembly 120 is positioned within the patient's blood vessel V (e.g., renal artery). The reference electrodes 200 may be positioned on the patient before, during, and/or after placement of the neuromodulation assembly 120 in the blood vessel V. In some embodiments, the neuromodulation assembly 120 may include first, second, third, and fourth ablation electrodes 124a-124d (referred to collectively as "ablation electrodes 124"), for example, as shown in FIG. 3. In other embodiments, however, the neuromodulation assembly 120 may include more or fewer ablation electrodes 124 (e.g., two ablation electrodes, three ablation electrodes, five ablation electrodes, six ablation electrodes, etc.). Although the reference electrodes 200 are shown positioned at the abdomen and upper leg region of the patient, in some embodiments one or more of the reference electrodes 200 may be positioned elsewhere on the patient's body, such as the patient's arms, lower legs, and upper torso, as well as at the backside of the patient. Moreover, any number of reference electrodes 200 may be used to achieve a desired energy delivery profile, such as one reference electrode, two reference electrodes, five reference electrodes, 15 reference electrodes, 30 reference electrodes, 100 reference electrodes, etc. Other related neuromodulation systems and methods are described in U.S. Provisional Patent Application No. 62/588,215, filed Nov. 17, 2017, the disclosure of which is incorporated herein by reference in its entirety.

Reference electrodes 200 may be relatively remote from ablation electrodes 124. For example, reference electrodes 200 may be adjacent a skin of the patient, while ablation electrodes 124 may be positioned within vasculature or a tissue site of the patient. Reference electrodes 200 may be used to complete a conductive path for monopolar stimulation delivered by one of ablation electrodes 124. In a monopolar mode, one or more electrodes of ablation electrodes 124 may be used to deliver stimulation, with one or more of reference electrodes providing a conductive path, for example, a return path. In some examples, the monopolar electric field from ablation electrodes 124 may be in-phase and all of the energy sent via the reference electrodes. Thus, the conductive path may be relatively long, and extend between one electrode of ablation electrodes 124 and at least one of reference electrodes 200. In contrast, in bipolar mode, reference electrodes 200 may not be used to provide a conductive path. For example, two electrodes of ablation electrodes 124 may be used to deliver bipolar stimulation, with reference electrodes 200 not being used for bipolar stimulation. In bipolar mode, the stimulation field may be generated between and adjacent to the two electrodes of ablation electrodes 124, and the conductive path may be relative short between the two electrodes of ablation electrodes 124 compared to the conductive path in a monopolar mode.

One general issue associated with renal neuromodulation is that tissue surrounding the target renal sites can vary from patient to patient, and therefore can respond differently to a given ablation energy. For example, renal tissues for different patients can have different electrical properties, thermal properties, thicknesses, and/or configurations. Furthermore, renal tissue can also vary for an individual patient, thereby causing the impedance field at the neuromodulation site to be irregular or non-uniform. As such, the effectiveness of renal neuromodulation across multiple patients can vary, and can lead to non-uniform lesions. To address these issues, some embodiments of the present technology are directed to delivering renal neuromodulation therapy that is tailored to an individual patient. Such techniques are expected to provide that a more uniform lesion can be created. For example, in some embodiments, pre-procedural steps and/or analysis (e.g., imaging and/or modeling) of a patient's renal area are performed prior to delivering neuromodulation and are used to optimize treatment for the individual patient.

In some embodiments, a target renal neuromodulation site may be preconditioned prior to ablation. For example, in some embodiments an electrically conductive material (e.g., saline) may be injected at or into the target site prior to ablation to create a local impedance field that is more uniform. The uniform or generally uniform impedance field is expected to allow the tissue at the target site to respond more consistently to a given ablation energy. In other embodiments, injecting an electrically insulative material (e.g., ethanol) can have a similar effect. The electrically conductive or insulative material can be injected via the same device delivering the ablation energy, or via a different device. Other materials that have similar electrically conductive or insulative properties, and that meet biocompatible standards, may also be injected and used in this manner. In some examples, the injected material may make tissue more or less susceptible to RF energy.

Figure 4B:
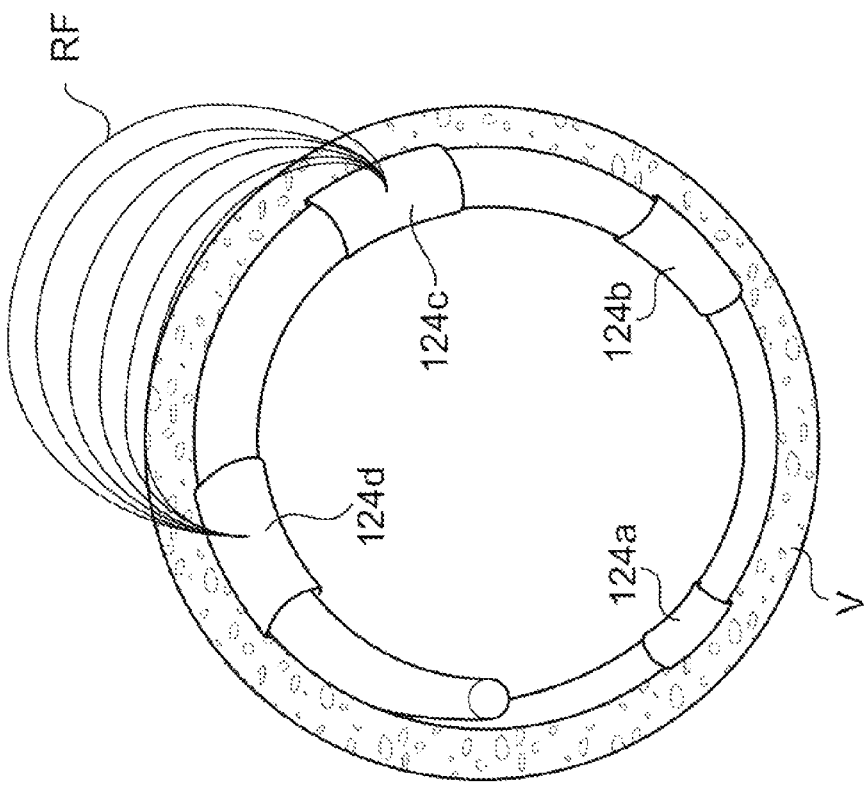
FIG. 4B illustrates a partially schematic end view of the neuromodulation assembly, in accordance with some embodiments of the present technology.
Figure 4A:
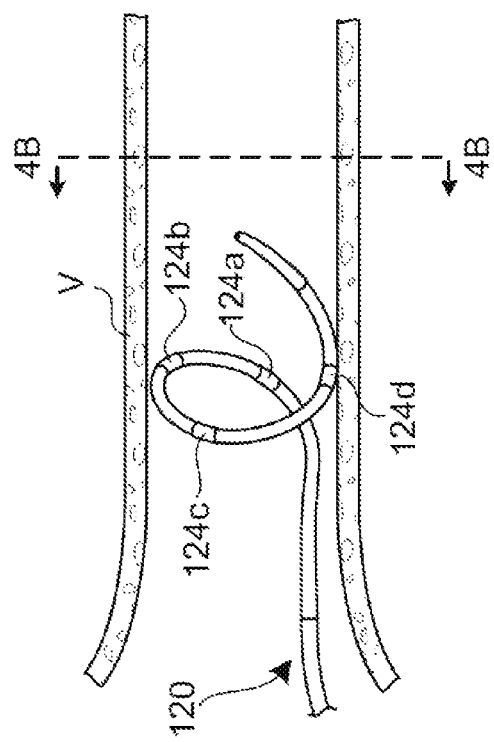
FIG. 4A illustrates a partially schematic side view of a neuromodulation assembly.

FIG. 4A illustrates a partially schematic side view of the neuromodulation assembly 120, and FIG. 4B illustrates a partially schematic end view of the neuromodulation assembly 120 taken along line 4B-4B of FIG. 4A. While FIGS. 4A and 4B are meant to represent the same neuromodulation assembly 120, certain features (e.g., electric fields) are only shown on FIG. 4B for illustrative purposes. As shown in FIG. 4B, the shape of the electrical field (e.g., RF field) can be modified by delivering energy in a bipolar mode via a pair of coupled ablation electrodes. The coupled electrodes can be adjacent to one another (e.g., first and second ablation electrodes 124a, 124b, second and third ablation electrodes 124b, 124c, or third and fourth ablation electrodes 124c, 124d), or non-adjacent to one another (e.g., first and third ablation electrodes 124a, 124c, second and fourth ablation electrodes 124b, 124d, or first and fourth ablation electrodes 124a, 124d). Each combination of coupled ablation electrodes can be selected to provide a RF field having a particular shape and/or direction to create a desired lesion. For example, referring to FIG. 4A, selecting the first and second ablation electrodes 124a, 124b can produce an RF field emanating from the neuromodulation assembly 120 in a direction that is into the plane of FIG. 4A, and selecting the second and third ablation electrodes 124b, 124c can produce an RF field emanating from the neuromodulation assembly 120 in a direction that is upward and partially out of the plane of FIG. 4A. Selecting non-adjacent electrodes, such as the first and third ablation electrodes 124a, 124c or the second and fourth ablation electrodes 124b, 124c, can similarly produce RF fields emanating from the neuromodulation assembly 120 in distinct directions. The ability to select different combinations of ablation electrodes 124 can be used in tandem with the selection of other signal delivery parameters of the electrical signal, such as frequency, amplitude, duty cycle, pulse interval, etc., to further influence the depth of an ablation and/or the shape of a lesion created therefrom.

Compared to delivering energy in a monopolar mode, where only a single ablation electrode (e.g., first ablation electrode 124a) is utilized, delivering energy in a bipolar mode can generate a more shallow RF field that is longitudinally spread between the two ablation electrodes and emanates outwardly from the neuromodulation assembly 120 to the surrounding vessel V. In practice, the controller 114 (FIG. 1) can cause delivery of ablation energy to be switched from a monopolar mode to a cycling bipolar mode in which RF fields are sequentially generated, for example, via the first and second ablation electrodes 124a, 124b, the second and third ablation electrodes 124b, 124c, and the third and fourth ablation electrodes 124c, 124d. Each combination or coupled pair of ablation electrodes 124 can comprise its own electrical circuit or can be part of a common single circuit connected in series.

Delivering bipolar energy via a coupled pair of ablation electrodes may also be done in connection with electrode interrogation that is performed prior to delivering the ablation energy. For example, in some embodiments, an electrical signal (e.g., electrical current) may be generated via the console 104 (FIG. 1) to determine the distances between the ablation electrodes 124. Depending on any difference in distances between coupled pairs of ablation electrodes, the power output used to generate the RF field for ablation can be adjusted to help ensure a similar RF field intensity is achieved for each coupled pair of ablation electrodes to realize a more uniform lesion.

In some examples, ablation electrodes 124 may be used to deliver an RF energy field configured to ablate nerves at or adjacent a target tissue site, and another set of electrodes, for example, non-ablation electrodes or secondary electrodes, may be used to deliver a non-RF energy field configured to avoid ablating the nerves (or other tissue) at or adjacent the target tissue site. The non-RF energy may also guide the RF field by reducing or preventing transmission of the RF field beyond the non-RF field. Instead of, or in addition to, using RF and non-RF fields, in some examples, a medical device may deliver alternating cycles of monopolar and bipolar stimulation via ablation electrodes 124. For example, the monopolar cycles may include relatively deeper fields, while the bipolar cycles may include relatively shallower fields. Thus, the extent of volume of influence of ablation electrodes 124 may be varied by such cycling.

FIGS. 5A and 5B illustrate another embodiment of the neuromodulation assembly 120, with FIG. 5A illustrating a partially schematic side view of the neuromodulation assembly 120, and FIG. 5B illustrating a partially schematic end view of the neuromodulation assembly 120. While FIGS. 5A and 5B are meant to represent the same neuromodulation assembly 120, certain features (e.g., the electric fields) are only shown on one of FIG. 5A or 5B for illustrative purposes. Referring to FIGS. 5A and 5B together, the neuromodulation assembly 120 can include a plurality of secondary electrodes 125. In some examples, secondary electrodes 125 may be non-ablation electrodes 125 (e.g., non-RF electrodes or electrodes not producing an RF field in addition to the ablation electrodes 124 previously described. The non-ablation electrodes 125 can include first, second, third, and fourth non-ablation electrodes 125a-125d (referred to collectively as "non-ablation electrodes 125" or "secondary electrodes 125"), and can be positioned across the neuromodulation assembly 120, such as between adjacent ablation electrodes (e.g., first and second ablation electrodes 124a, 124b). The non-ablation electrodes 125 can each emit electrical energy at a non-RF frequency that does not directly cause permanent or semi-permanent alterations to the tissue. In addition, the non-ablation electrodes 125 can each act as return electrodes for each of the ablation electrodes 124. In such an embodiment, the neuromodulation assembly 120 can deliver a monopolar electric field via an electrical circuit comprising one of the ablation electrodes 124 and one of the non-ablation electrodes 125. Each combination of ablation electrodes 124 and non-ablation electrodes 125 can comprise its own electrical circuit.

In some embodiments, the combination of ablation electrodes 124 and non-ablation electrodes 125 can be automatically or manually selected to produce an RF field that has a desired direction and/or shape. For example, an electrical signal may be generated and used to determine the distances between individual ablation electrodes 124 or between the ablation electrodes 124 and the non-ablation electrodes 125. The determined distances can be used to further determine a general orientation of the ablation and non-ablation electrodes 124, 125 relative to one another. In such embodiments, the ablation electrodes 124 and non-ablation electrodes 125 may be selected based on their determined distances and/or orientations to emit an RF field in a desired direction. For example, as shown in FIG. 5A, the third ablation electrode 124c and the second non-ablation electrode 125b may be selected to emit an RF field $E_1$ in a direction that is upward and slightly out of the plane of FIG. 5A. Similarly, the third ablation electrode 124c and the third non-ablation electrode 125c may be selected to emit an RF field $E_2$ in a direction that is downward and slightly out of the plane of FIG. 5A. In some embodiments, the combination of ablation electrodes 124 and non-ablation electrodes 125 may also be selected based on measurements of the local impedance field, and/or other pre-procedural analysis.

While electrodes 124 may be ablation electrodes, and electrodes 125 may be non-ablation electrodes, in some examples, electrodes 124 may be primary electrodes 124 of a plurality of electrodes of catheter 102, and electrodes 125 may be secondary electrodes 125. Console 104, a programmer, a generator, or another medical device may deliver electrical signals via primary electrodes 124 and secondary electrodes 125 such that some or all of primary electrodes 124 or secondary electrodes 125 may deliver RF energy or non-RF energy.

In some examples, catheter 102 includes an electrode array including plurality of primary electrodes 124 spaced apart along an elongated member, and a plurality of secondary electrodes 125 spaced apart along the elongated member. A medical device, for example, console 104, or a generator, or any suitable medical device, may be electrically coupled to plurality of primary electrodes 12 and plurality of secondary electrodes 125. The medical device may be configured to generate and deliver a radiofrequency (RF) energy field via at least one primary electrode of plurality of primary electrodes 124. The RF energy field is configured to ablate nerves at or adjacent a target tissue site. The medical device may be configured to generate and deliver a non-RF energy field via at least one secondary electrode of plurality of secondary electrodes 125 substantially simultaneously with the RF energy field. The non-RF energy field is configured to avoid ablating the nerves at or adjacent the target tissue site. In some examples, the non-RF energy field is configured to avoid ablating nerves or other tissue adjacent the target tissue site.

In some examples, the non-RF energy field substantially inhibits the RF energy field from extending beyond the non-RF energy field. In some examples, the non-RF energy field is configured to guide the RF energy field to the nerves at or adjacent the target tissue site.

In some examples, plurality of primary electrodes 124 includes a coupled electrode pair including a first primary electrode and a second primary electrode proximate one another, and the RF energy field includes a bipolar RF energy field delivered via the first primary electrode and the second primary electrode of the coupled electrode pair. In some examples, the coupled electrode pair is a first coupled electrode pair, plurality of primary electrodes 124 includes a third primary electrode and a fourth primary electrode, plurality of primary electrodes 124 includes a second coupled electrode pair including the second primary electrode and the third primary electrode, plurality of primary electrodes 124 includes a third coupled electrode pair including the third primary electrode and the fourth primary electrode. The bipolar RF energy field may be a first bipolar RF energy field, and the medical device may be configured to generate and deliver the first bipolar RF energy field via the first coupled pair, a second bipolar RF field via the second coupled pair, and a third bipolar RF energy field via the third coupled pair.

In some examples, plurality of secondary electrodes 125 includes a first secondary electrode and a second secondary electrode spaced apart from the first secondary electrode. The first primary electrode may be positioned on the elongated member between the first and second secondary electrodes. The non-RF energy field may include a first non-RF energy field. The medical device may be configured to generate and deliver the first non-RF energy field via the first secondary electrode and generate and deliver a second non-RF energy field via the second secondary electrode. One or both of the first or the second non-RF energy fields substantially inhibit the bipolar RF energy field from extending beyond the first or second non-RF energy fields.

In some examples, at least one of the plurality of secondary electrodes differs in at least one electrode characteristic from at least one of the plurality of primary electrodes. In some examples, tissue adjacent the target tissue site includes injected electrically conductive material or injected electrically insulative material, and where the injected electrically conductive material or injected electrically insulative material causes a substantially uniform local impedance field at or adjacent the target tissue site.

In some examples, the disclosure describes an example technique including controlling, by a processor, the medical device to generate and deliver a radiofrequency (RF) energy field via at least one primary electrode of plurality of primary electrodes 124. The example technique includes controlling, by the processor, the medical device to generate and deliver a non-RF energy field via at least one secondary electrode of plurality of secondary electrodes 125 substantially simultaneously with the RF energy field. The non-RF energy field is configured to avoid ablating the nerves at or adjacent the target tissue site.

In addition to or in lieu of using the non-ablation electrodes 125 as part of the electrical circuit to produce an RF field, the non-ablation electrodes 125 may be used to guide the RF field generated by the ablation electrodes 124 without being part of the electrical circuit. As previously described, the non-ablation electrodes 125 can emit a non-RF field in a direction toward the vessel V and away from the neuromodulation assembly 120. In some embodiments, the emitted non-RF field from the non-ablation electrodes 125 can inhibit or partially prevent an emitted RF field from traveling past the non-RF field. As such, the emitted non-RF field can act as a guide or virtual "wall" that directs or maintains an emitted RF field along a desired path. For example, as shown in FIG. 5B, the first non-ablation electrode 125*a* emits a first non-RF field $F_1$, and the second non-ablation electrode 125*b* emits a second non-RF field $F_2$ spaced apart from the first non-RF field $F_1$. The ablation electrode 124*b* is positioned between the first and second non-ablation electrodes 125*a*, 125*b*, and emits an RF field that is generally guided by the first and second non-RF fields $F_1$, $F_2$, and maintained therebetween. Stated another way, the first and second non-RF fields $F_1$, $F_2$, inhibit or partially prevent the RF field from traveling beyond the first and second non-RF fields $F_1$, $F_2$. In practice, using emitted non-RF fields in this manner to can offer a clinician or operator more control of the shape of a lesion and/or the depth of ablation. Additionally, using non-RF and RF fields in tandem can better concentrate the ablative energy from the RF field on the targeted nerves, and thereby improve efficacy of neuromodulation treatment while minimizing/inhibiting the delivery of ablative energy to non-target tissue. Moreover, using non-RF and RF fields in tandem is expected to allow the RF field to be more precisely directed and contained, while also decreasing required power output from the signal generator.

System 100 may include a reference electrode. A medical device, for example, console 104, or a generator, or any suitable medical device, may be electrically coupled to plurality of primary electrodes 124 and to the reference electrode. The medical device may be configured to generate and deliver a plurality of monopolar cycles of a monopolar radiofrequency (RF) energy field via a monopolar electrode pair including a primary electrode of the plurality of primary electrodes 124 and the reference electrode. The monopolar RF energy field has a first volume of influence at or adjacent a target tissue site. The medical device may be configured to generate and deliver a plurality of bipolar cycles of a bipolar RF energy field via at least one bipolar electrode pair including two primary electrodes of the plurality of primary electrodes 124. The bipolar RF energy field has a second volume of influence smaller than the first volume of influence at or adjacent the target tissue site. The medical device is configured to generate and deliver a plurality of alternating cycles including the plurality of the monopolar cycles and the plurality of bipolar cycles.

In some examples, the primary electrode of the monopolar pair includes a first primary electrode of the plurality of primary electrodes 124, and the two primary electrodes of the bipolar electrode pair include a second primary electrode and a third primary electrode of the plurality of primary electrodes 124. In some examples, the two primary electrodes of the bipolar electrode pair include the primary electrode of the monopolar pair.

In some examples, the number of the plurality of the bipolar cycles is less than 50% of the number of the plurality of monopolar cycles. In some examples, the number of the plurality of the bipolar cycles is less than 10% of the number of the plurality of monopolar cycles.

In some examples, the at least one bipolar electrode pair includes a first bipolar electrode pair, a second bipolar pair, and a third bipolar pair. In some such examples, the medical device is configured to generate and deliver the plurality of bipolar cycles via, in sequence, the first bipolar electrode pair, the second bipolar electrode pair, and the third bipolar electrode pair.

In some examples, plurality of primary electrodes 124 comprises a sequence of a first primary electrode, a second primary electrode, a third primary electrode, and a fourth primary electrode along the elongated member. The first bipolar electrode pair includes the first primary electrode and the second primary electrode, the second bipolar electrode pair includes the second primary electrode and the third primary electrode, and the third bipolar electrode pair includes the third primary electrode and the fourth primary electrode.

In some examples, plurality of primary electrodes 124 comprises a sequence of a first primary electrode, a second primary electrode, a third primary electrode, and a fourth primary electrode along the elongated member. The first bipolar electrode pair includes the first primary electrode and the third primary electrode, the second bipolar electrode pair includes the second primary electrode and the fourth primary electrode, and the third bipolar electrode pair includes the first primary electrode and the fourth primary electrode.

In some examples, an example technique includes generating, by a processor, for delivery via a medical device, a plurality of monopolar cycles of a monopolar radiofrequency (RF) energy field via a monopolar electrode pair including a primary electrode of plurality of primary electrodes 124 and the reference electrode. The example technique includes generating, by the processor, for delivery via the medical device, a plurality of bipolar cycles of a bipolar RF energy field via at least one bipolar electrode pair including two primary electrodes of plurality of primary electrodes 124. The example technique includes generating, by the processor, for delivery via the medical device, a plurality of alternating cycles including the plurality of the monopolar cycles and the plurality of bipolar cycles.

Figure 6B:
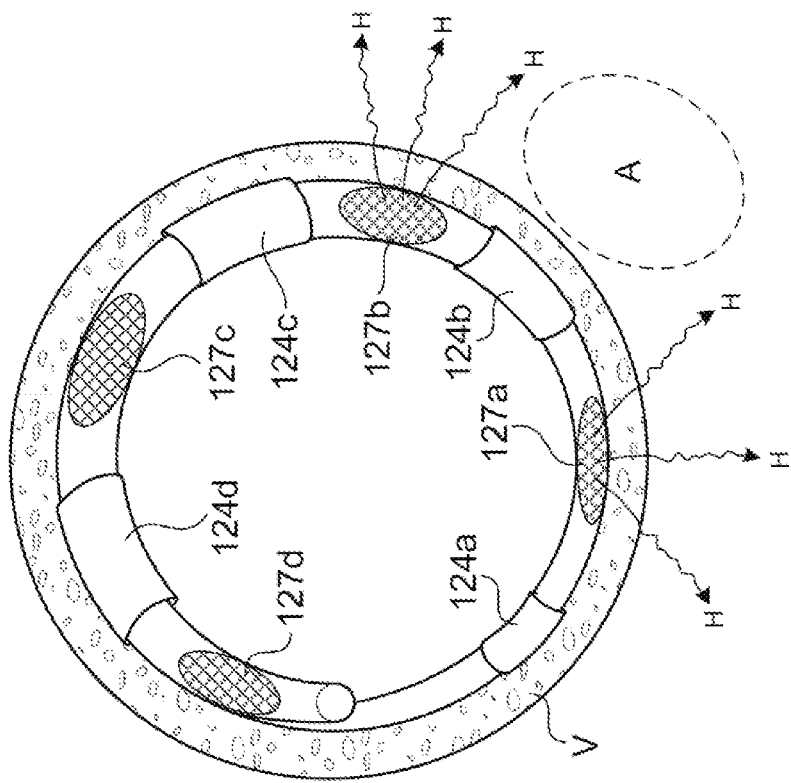
FIG. 6B illustrates a partially schematic end view of the neuromodulation assembly, in accordance with some embodiments of the present technology.
Figure 6A:
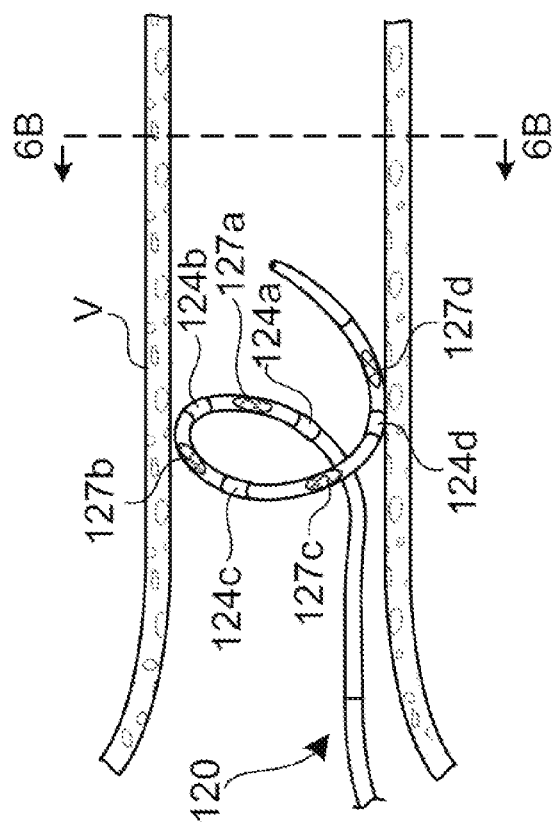
FIG. 6A illustrates a partially schematic side view of a neuromodulation assembly.

FIGS. 6A and 6B illustrate another embodiment of the neuromodulation assembly 120, with FIG. 6A illustrating a partially schematic side view of the neuromodulation assembly 120, and FIG. 6B illustrating a partially schematic end view of the neuromodulation assembly taken along line 6B-6B of FIG. 6A. While FIGS. 6A and 6B are meant to represent the same neuromodulation assembly 120, certain features (e.g., heat streams) are only shown on FIG. 6B for illustrative purposes. Referring to FIGS. 6A and 6B together, the neuromodulation assembly 120 can include a plurality of thermal elements 127 that can be used to affect the thermal field of the vessel V surrounding neuromodulation assembly 120. The thermal elements 127 can include first, second, third, and fourth thermal elements 127a-127d (referred to collectively as "thermal elements 127"). The thermal elements 127 can be positioned across the neuromodulation assembly 120, such as between adjacent ablation electrodes 124 (e.g., first and second ablation electrodes 124a,b). The thermal elements 127 can include conductive or insulative elements that provide thermal heating effects to the surrounding areas.

Desired thermal heating effects may include modifying the thermal field of a particular tissue or target site without altering the electric field. For example, in some embodiments the thermal elements 127 can raise the temperature of target neural fibers to be above a desired threshold to condition the tissue for ablation or to achieve non-ablative thermal alteration. In such an embodiment, the temperature of the target neural fibers may be raised to be above body temperature (e.g., about 37° C.) but less than about 45° C. for non-ablative thermal alteration. As shown in FIG. 6B, the thermal elements 127 can heat areas immediately surrounding the outer walls of the vessel V, as indicated by heat streams H. The heat streams H can be controlled to not ablate the surrounding tissue, but instead preheat the tissue around a target site to saturate the tissue with thermal energy without causing damage. In such an embodiment, an RF field could then be directed to the targeted site to cause the desired ablation with less power output required, since the tissue will have already been preheated to a temperature just below that required for thermal ablation.

In addition to or in lieu of the foregoing, the thermal elements 127 can also be used to selectively direct a pathway of a thermal field in a desired direction. For example, without being bound by theory of thermodynamics, a thermal field will naturally flow from hot to cold areas until temperature becomes approximately equal. Using these principles of thermodynamics, the thermal elements 127 can be used to selectively heat areas immediately surrounding a desired pathway to help guide a thermal and/or electric field that is subsequently generated. For example, as shown in FIG. 6B, the heat streams H can heat the areas surrounding zone A to help guide an electric and/or thermal field subsequently generated by the ablation electrode 124b. The hotter thermal field surrounding zone A can help focus the electric and/or thermal field to zone A.

Figure 7:
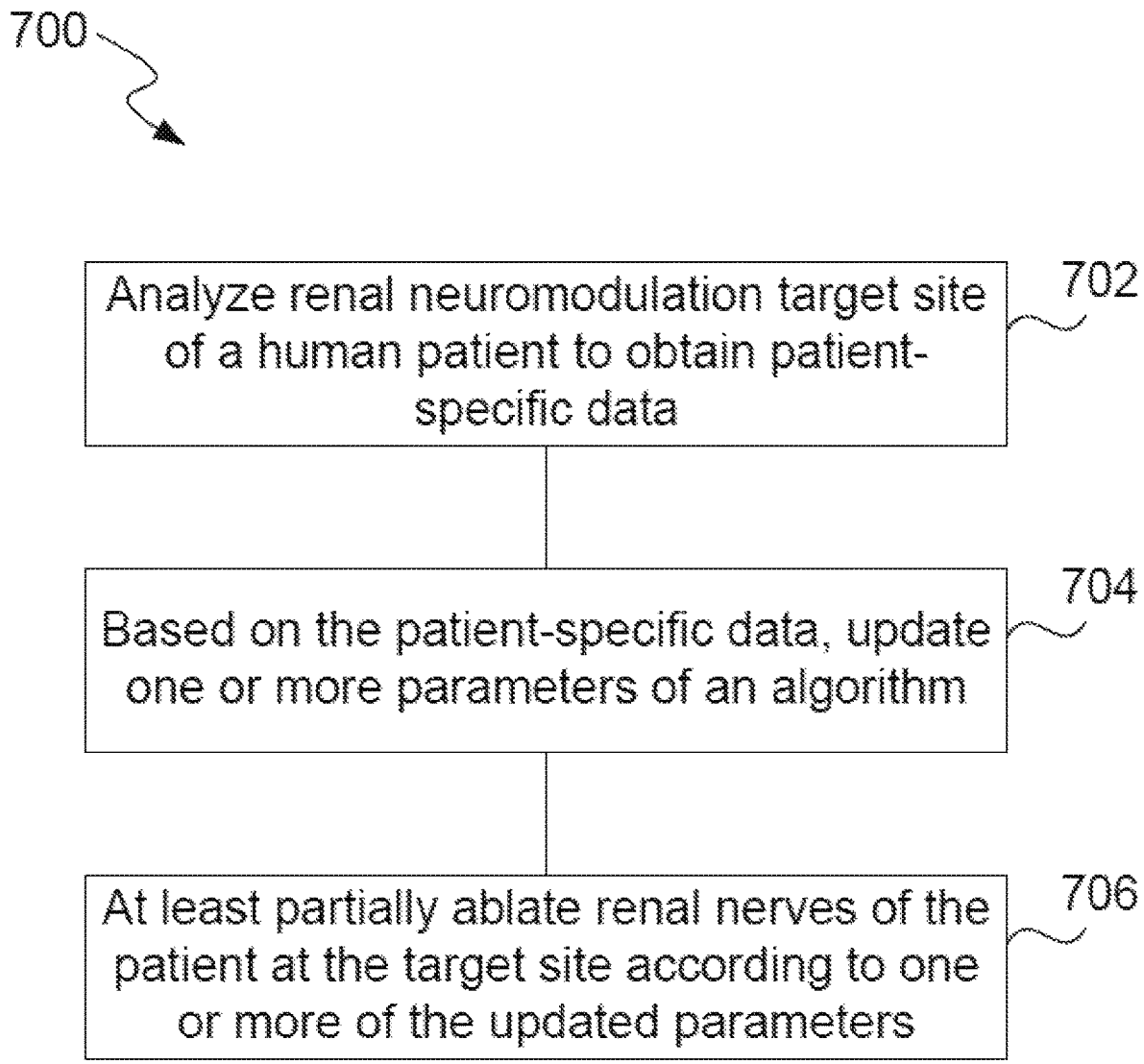
FIG. 7 is a block diagram illustrating a method of using ablation electrodes in accordance with some embodiments of the present technology.

FIG. 7 is a block diagram illustrating a method 700 of using ablation electrodes in accordance with some embodiments of the present technology. More specifically, method 700 includes gathering patient-specific data that is obtained prior to delivering neuromodulation treatment and used to alter or update an algorithm utilized to deliver neuromodulation treatment. According to some methods of the present technology, a renal neuromodulation area or target site of a human patient is analyzed to obtain patient-specific data related to the renal neuromodulation target site (block 702). The patient-specific data relates to the renal neuromodulation area to be treated, and can include details of the patient's renal tissue, including its electrical properties, thermal properties, thickness, and general configuration. Accordingly, analyzing the patient can include methods and techniques used to gather such patient-specific data. For example, analyzing the patient can include imaging, modeling, and/or mapping of the patient's renal neuromodulation area. In addition, the patient-specific data can also relate to the positioning of a neuromodulation assembly within a vessel of the patient, such as the distance(s) between one or more of the ablation electrodes (e.g., ablation electrodes 124). In such an embodiment, analyzing the patient can include performing electrode interrogation (as previously described with reference to FIGS. 4A and 4B). In yet other embodiments, analyzing the patient can include determining impedance data of the combination of different ablation electrodes, other non-ablation electrodes (e.g., non-ablation electrodes 125), and/or other elements (e.g., thermal elements 127) on the neuromodulation assembly 120. In addition to or in lieu of the foregoing, other measurements, such as a temperature at one or more of the ablation electrodes 124 or blood chemistry, may also obtained. Analyzing the patient can be performed at set times, or on a continuous basis even as the patient is receiving treatment.

Based on the patient-specific data obtained, one or more parameters of an algorithm for delivering renal neuromodulation treatment can be updated accordingly (block 704). The updated algorithm can be used for delivering renal neuromodulation treatment via one or more energy delivery elements of a renal neuromodulation catheter (e.g., neuromodulation catheter 102). Prior to being updated, the algorithm may be a base or standard algorithm having parameters (e.g., predetermined parameters) provided for delivering neuromodulation treatment. The standard algorithm may be one of multiple available standard algorithms, and may be chosen according to the symptoms and/or characteristics of the particular patient being treated. Once updated, the algorithm can transition from being a standard algorithm used generally for any patient, to a tailored algorithm used for the particular patient. The parameters of the algorithm can include frequency, amplitude, duty cycles, pulse intervals, or other parameters commonly used to deliver neuromodulation treatment. The updated parameters of the algorithm can be used to at least partially ablate renal nerves of the patient at the renal neuromodulation target site via energy from one or more of the energy delivery elements (block 706).

In some embodiments, the operations associated with blocks 702, 704, and 706 can be iteratively repeated in a closed loop manner. For example, after at least partially ablating the renal nerves of the patient according to the algorithm having a first set of parameters (e.g., block 706), the method 700 may return to block 702 to re-analyze the renal neuromodulation target site to obtain updated patient-specific data. The algorithm can then be further updated with a second set of parameters based on the updated patient-specific data (block 704), and renal nerves of the patient can be at least partially ablated by delivering energy according to the second set of parameters (block 706). This closed loop can be repeated to further optimize neuromodulation treatment for the particular patient.

Delivering neuromodulation treatment to patients in the manner described in method 700 can help optimize treatment for each patient. As previously described, a general issue associated with delivering neuromodulation therapy is that tissue surrounding the renal neuromodulation areas can vary from patient to patient, and even individual patients. As such, each localized tissue area can respond differently to a given ablation energy and can cause non-uniform lesions. The present technology, including the operations of method 700 described herein, helps address this issue by tailoring neuromodulation treatment according to patient-specific data related to tissue configuration and characteristics. Accordingly, the present technology can improve the effectiveness of neuromodulation treatment, and optimize delivery of neuromodulation treatment by, for example, decreasing power output needed to achieve a desired lesion.

The following discussion provides further details regarding patient anatomy and physiology as it may relate to renal denervation therapy. This section is intended to supplement and expand upon the previous discussion regarding the relevant anatomy and physiology, and to provide additional context regarding the disclosed technology and the therapeutic benefits associated with renal denervation. For example, several properties of the renal vasculature may inform the design of treatment devices and associated methods for achieving renal neuromodulation via intravascular access, and impose specific design requirements for such devices. Specific design requirements may include accessing the renal artery, facilitating stable contact between the energy delivery elements of a therapy delivery device and a luminal surface or wall of the renal artery, and/or effectively modulating the renal nerves with the therapy delivery device.

As noted previously, the sympathetic nervous system (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to physiological features as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

Figure 8:
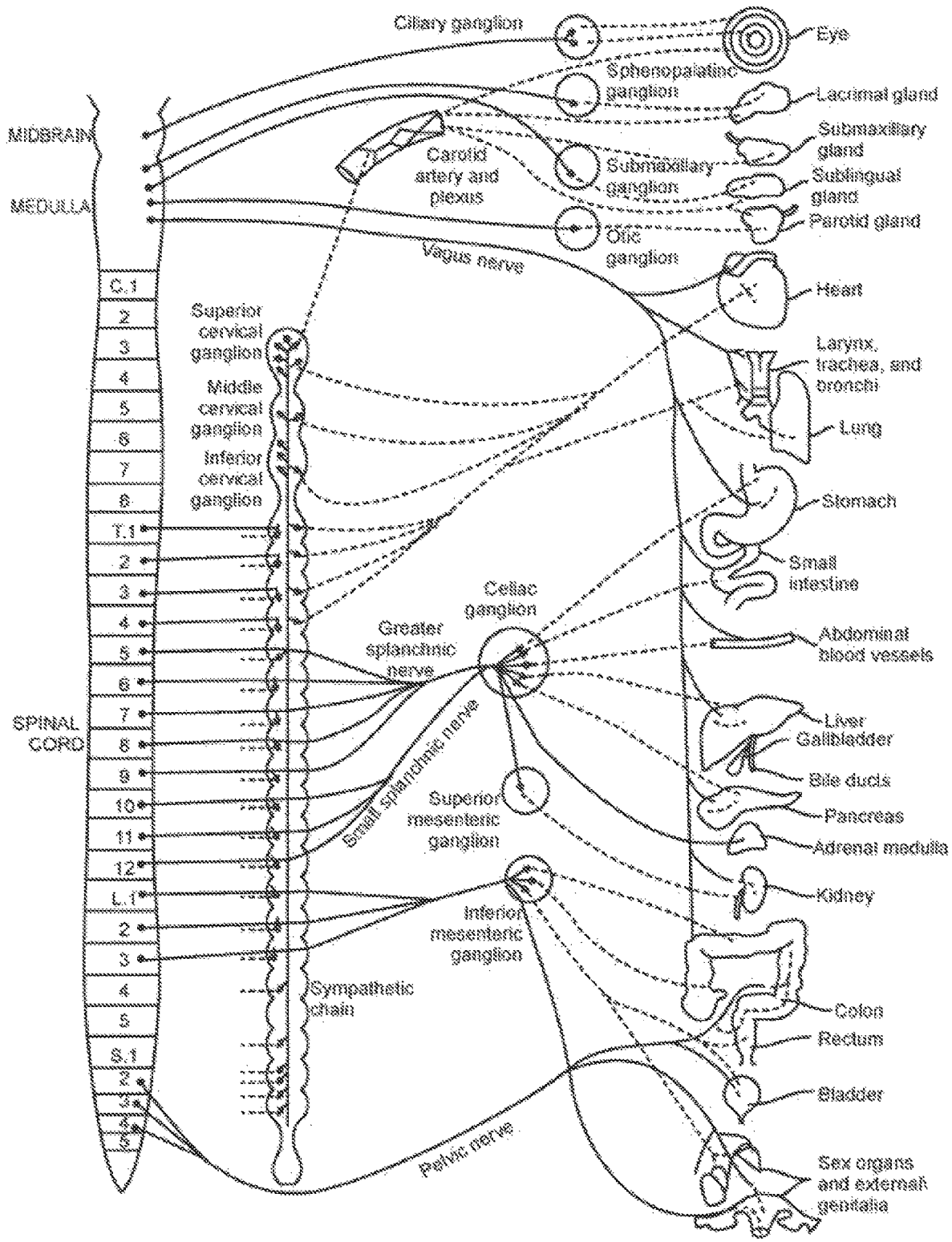
FIG. 8 is a conceptual illustration of the sympathetic nervous system (SNS) and how the brain communicates with the body via the SNS.

As shown in FIG. 8, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia, discussed above. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

Figure 9:
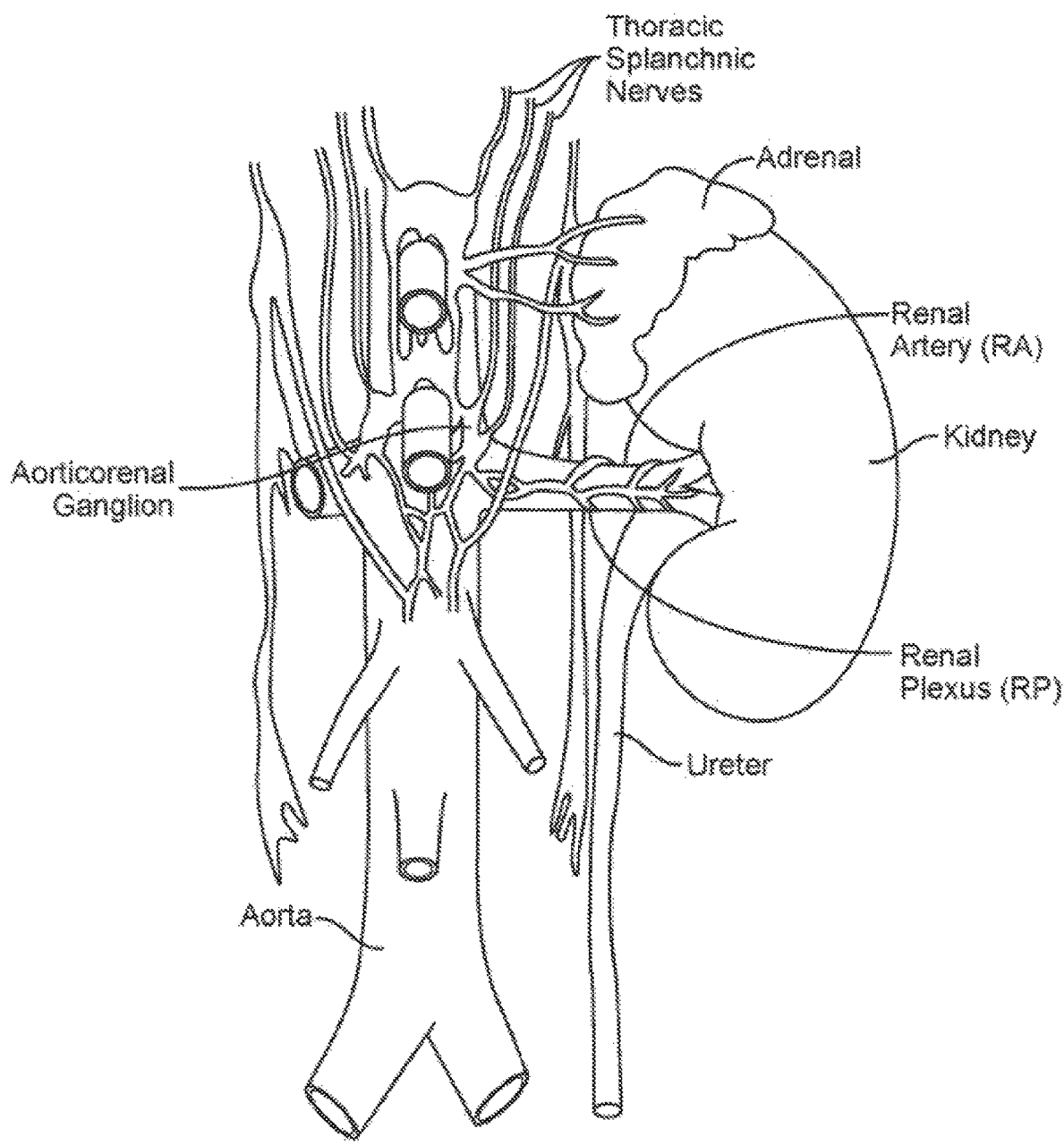
FIG. 9 is an enlarged anatomic view of nerves innervating a left kidney to form the renal plexus surrounding the left renal artery.

As FIG. 9 shows, the kidney is innervated by the renal plexus (RP), which is intimately associated with the renal artery. The renal plexus (RP) is an autonomic plexus that surrounds the renal artery and is embedded within the adventitia of the renal artery. The renal plexus (RP) extends along the renal artery until it arrives at the substance of the kidney. Fibers contributing to the renal plexus (RP) arise from the celiac ganglion, the superior mesenteric ganglion, the aorticorenal ganglion and the aortic plexus. The renal plexus (RP), also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus (RP) and are distributed to the renal vasculature.

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well-known adverse consequences of chronic sympathetic over activity, such as hypertension, left ventricular hypertrophy, ventricular arrhythmias, sudden cardiac death, insulin resistance, diabetes, and metabolic syndrome.

Sympathetic nerves to the kidneys terminate in the blood vessels, the juxtaglomerular apparatus and the renal tubules. Stimulation of the renal sympathetic nerves causes increased renin release, increased sodium ($Na^r$) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

Figure 10:
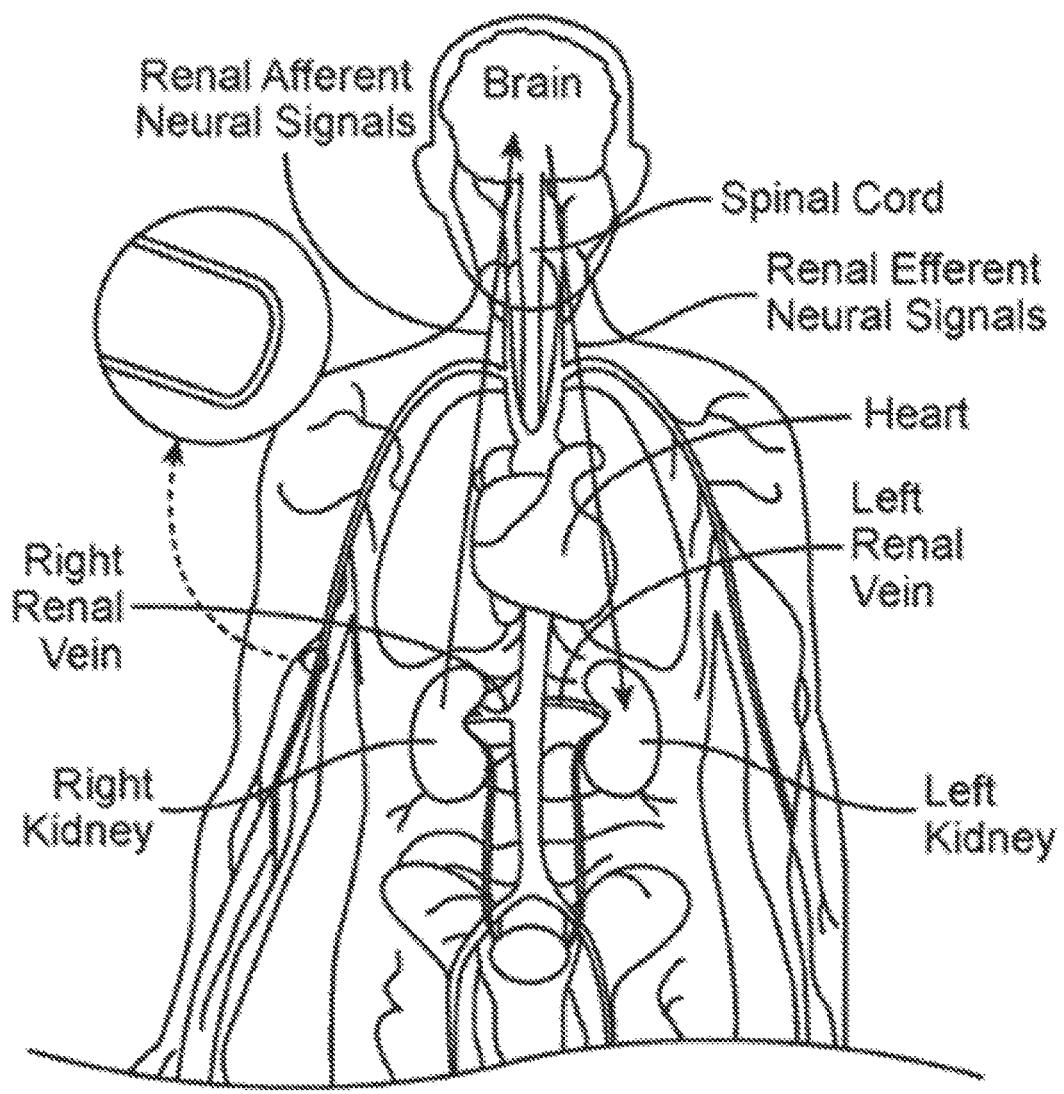
FIGS. 10 and 11 are anatomic and conceptual views, respectively, of a human body depicting neural efferent and afferent communication between the brain and kidneys.
Figure 11:
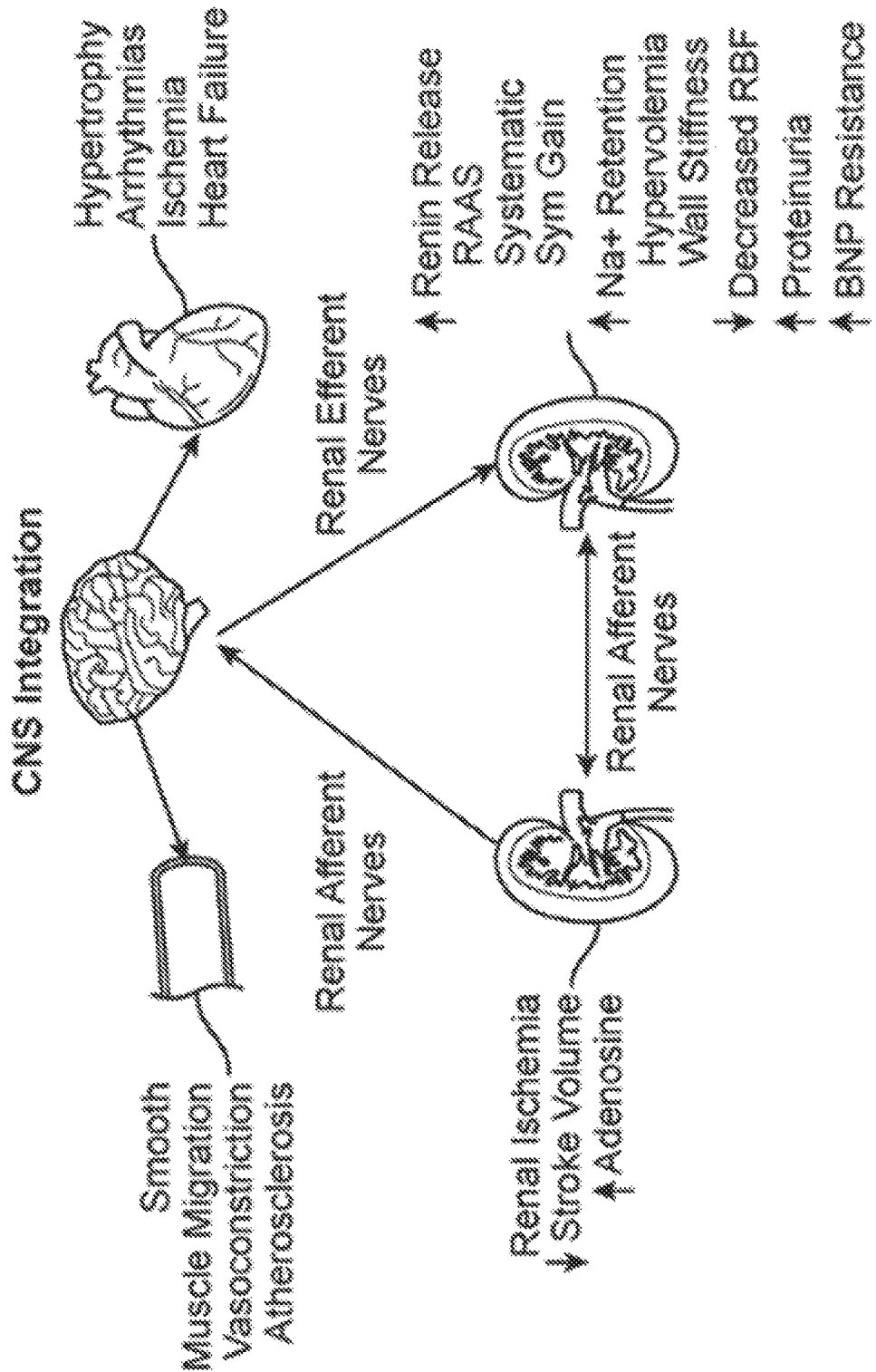

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 10 and 11, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 8. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

Figure 12:
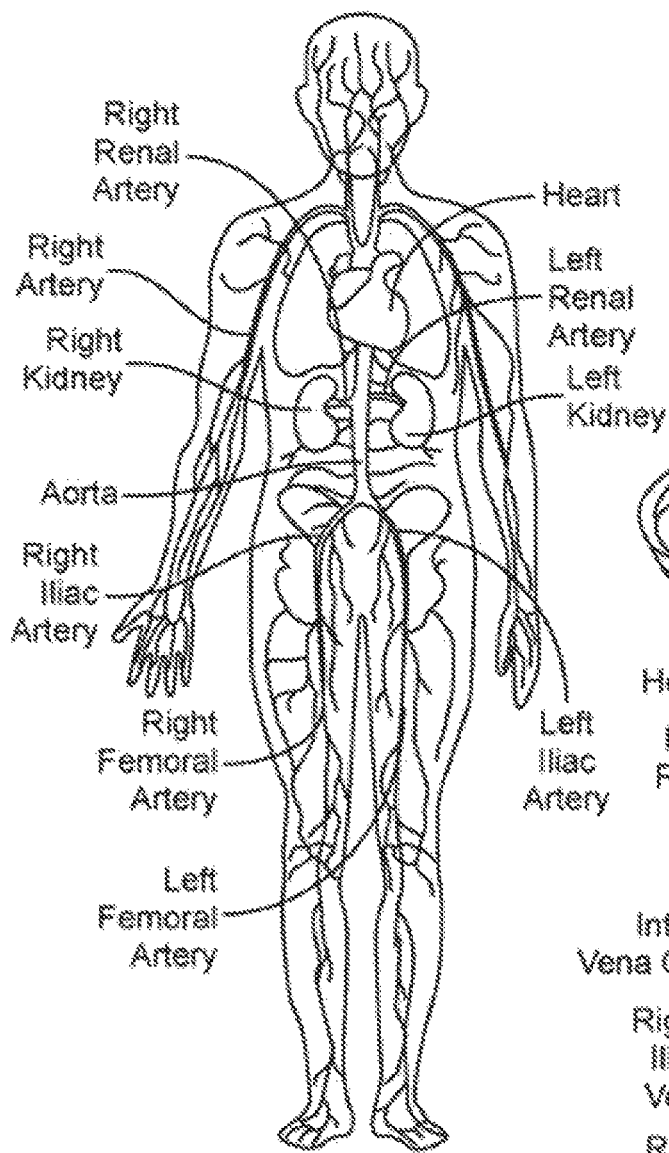
FIGS. 12 and 13 are anatomic views of the arterial vasculature and venous vasculature, respectively, of a human.

In accordance with the present technology, neuromodulation of a left and/or right renal plexus (RP), which is intimately associated with a left and/or right renal artery, may be achieved through intravascular access. As FIG. 12 shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 13:
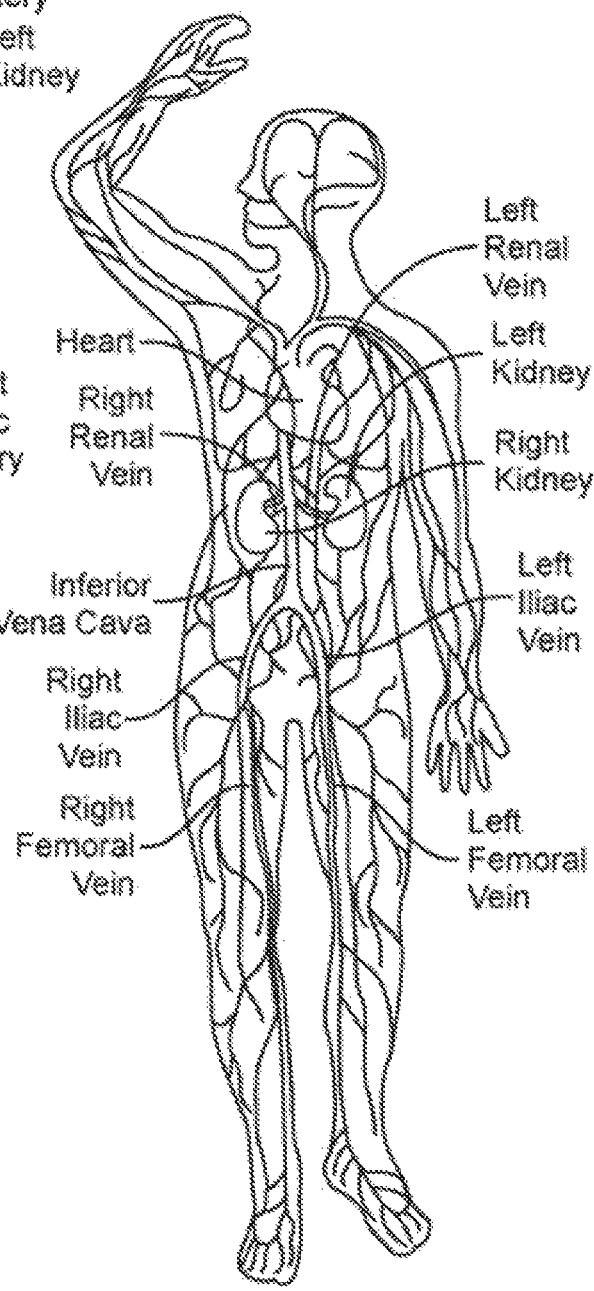

As FIG. 13 shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

Since neuromodulation of a left and/or right renal plexus (RP) may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. For example, navigation can be impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e. cause the wall of the artery to pulse).

Even after accessing a renal artery and facilitating stable contact between neuromodulatory apparatus and a luminal surface of the artery, nerves in and around the adventia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, a full-circle lesion likely resulting from a continuous circumferential treatment may be potentially related to renal artery stenosis. Therefore, the formation of more complex lesions along a longitudinal dimension of the renal artery and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided because to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility; and (f) the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, DRA, typically is in a range of about 2-10 mm, with most of the patient population having a DRA of about 4 mm to about 8 mm and an average of about 6 mm. Renal artery vessel length, LRA, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta induced by respiration and/or blood flow pulsatility. A patient's kidney, which is located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the energy delivery element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments. All references cited herein are incorporated by reference as if fully set forth herein.

From the foregoing, it will be appreciated that specific embodiments of the present disclosure have been described herein for purposes of illustration, but that various modifications may be made without deviating from the present disclosure. For example, while particular features of the neuromodulation assembly 120, including the non-ablation electrodes 125, and the thermal elements 127, were described as being part of a single device, in other embodiments, these features can be included on one or more separate devices that can be positioned adjacent to and/or used in tandem with the neuromodulation assembly 120 to perform similar functions to those described herein. Additionally, while the description of the present technology is focused on generating RF fields, the present technology can equally be applied to other methods of energy delivery, including ultrasonic, cryogenic, direct heating, and other heating/cooling methods known in the relevant art.

Certain aspects of the present disclosure described in the context of particular embodiments may be combined or eliminated in other embodiments. For example, the bipolar energy delivery described with reference to FIGS. 4A and 4B, non-ablation electrodes 125 described with reference to FIGS. 5A and 5B, and the thermal elements 127 described in reference to FIGS. 6A and 6B, can be combined with one another in still further embodiments. Additionally, the method 700 described with reference to FIG. 7, wherein patient-specific data is obtained and used to deliver neuromodulation treatment to a particular patient, can be utilized in conjunction with the non-ablation electrodes 125 described with reference to FIGS. 5A and 5B, and/or the thermal elements 127 described in reference to FIGS. 6A and 6B. Further, while advantages associated with certain embodiments have been described in the context of those embodiments, other embodiments may also exhibit such advantages, and not all embodiments need necessarily exhibit such advantages to fall within the scope of the present disclosure. Accordingly, the present disclosure and associated technology can encompass other embodiments not expressly shown or described herein.

As discussed above, therapeutic efficacy for some medical procedures, such as renal denervation, may be achieved by generating and delivering a radiofrequency (RF) energy field and a non-RF energy field. In some examples, therapy delivery by example electrodes, electrode arrays, and catheters according to the disclosure may be modeled using computer models, for example, computer models that incorporate patient-specific data or tissue parameter data to determine electric fields and volumes of influence generated by different configurations of electrode arrays or different types of catheters or other therapy delivery devices, as described with reference to FIGS. 14 to 20. The computer modeling may be used to select a particular catheter (and, therefore, a particular electrode array configuration) for therapy delivery and/or to determine, for a given electrode array and patient anatomy, the electrical signal parameters of therapy (e.g., denervation therapy) expected to provide efficacious results. While denervation therapy (also referred as neuromodulation therapy) is primarily described with reference to the modeling in other examples, the devices, systems, and techniques described herein may be used with other types of therapy.

As discussed above, denervation therapy may include delivering electrical energy to a nerve in order to render the nerve inert, inactive, or otherwise completely or partially reduced in function. This complete or partial reduction in function may be temporary or permanent. As described with reference to FIGS. 14 to 20, some systems and techniques according to the disclosure may be used to estimate a volume of influence of a denervation stimulus delivered to a target nerve, and based on the volume of influence, to determine one or more parameters of denervation therapy. In some examples, the one or more parameters of denervation therapy determined based on the estimated volume of influence may be used to automatically control a medical device to deliver the denervation therapy to a patient. The volume of influence may be estimated based on a computer model generated from a digital reconstruction of a region of a patient, the digital reconstruction indicating parameters such as tissue types and relative locations. The volume of influence may be considered to be a volume within a predetermined region of a patient in which an applied denervation stimulation results in denervation, for example, by ablation or lesioning within the volume of influence. Thus, the viability of nerves in the volume of influence may be reduced below a predetermined threshold, so that the nerves in the volume of influence exhibit reduced, substantially reduced, or substantially no activity. In some examples, the denervation therapy may result in lesioning of the target nerve while avoiding lesioning of a predetermined adverse-effect region, for example, a non-target non-nerve tissue.

Devices, systems, and techniques for determining one or more parameters of denervation therapy using a computer model that takes into consideration patient-specific tissue characteristics and anatomy, tissue modification, as well as the configuration of an electrode array (e.g., electrodes of catheter 102), including the varying electrode characteristics of the electrodes, may be useful for determining one or more parameters of denervation therapy. In some examples, these parameters can include an electrical signal parameter, the electrodes of catheter 102 with which an electrical signal is delivered to the target tissue site, and, in some examples, the specific catheter used to deliver the denervation stimuli (which may inform the configuration of the electrodes). The one or more determined parameters of denervation therapy may be stored by a device, such as a medical device programmer or a medical device, as a therapy program, which may be used by the medical device to generate and deliver denervation therapy to a patient.

Figure 14:
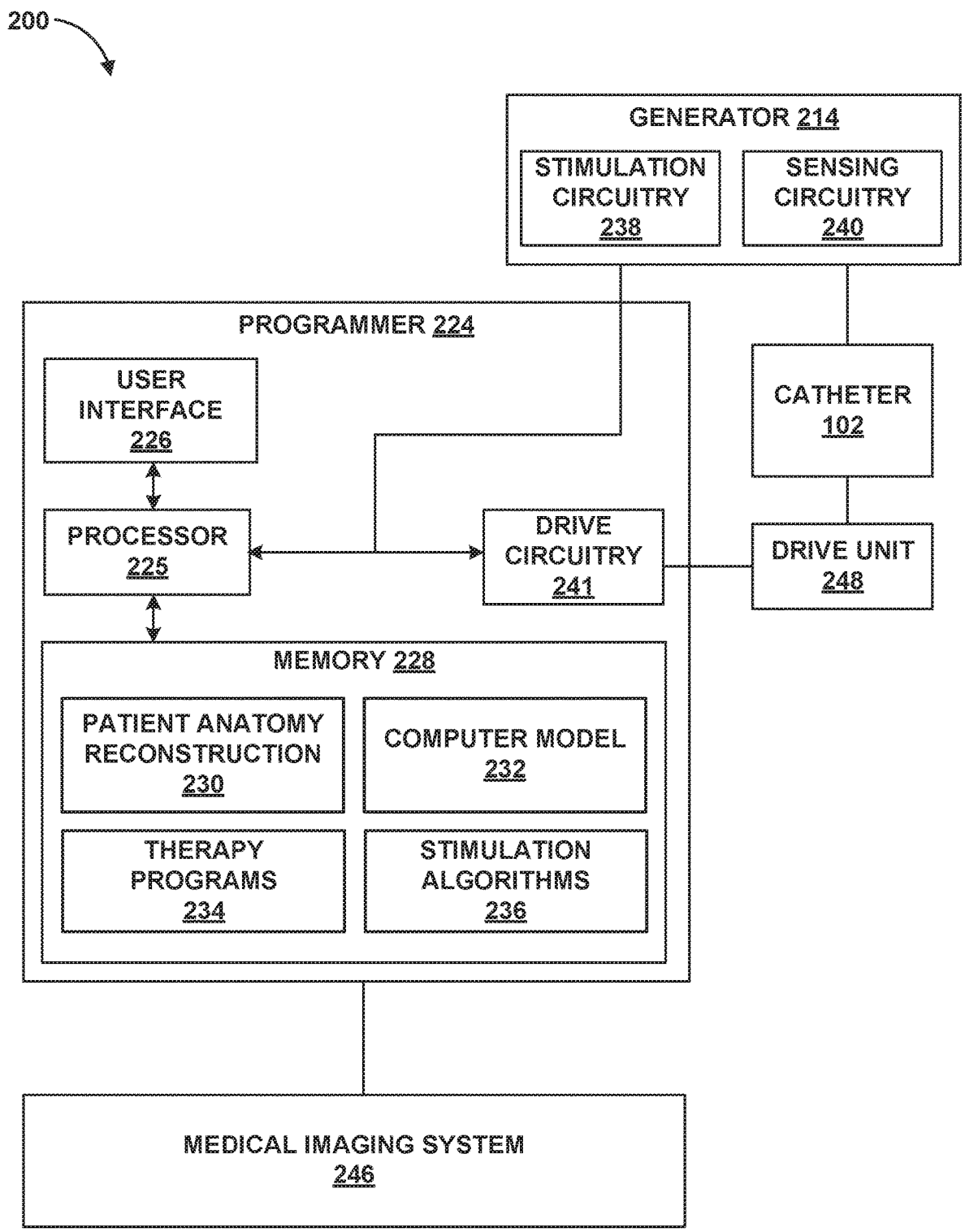
FIG. 14 is a schematic and conceptual illustration of a system including an example generator and an example programmer coupled to an imaging system and an example therapy delivery device.

The functioning of catheter 102 and generator 214 may be controlled by programmer 224 based on estimated volume of influence of denervation therapy. For example, programmer 224 may determine one or more therapy parameters for a therapy program for achieving predetermined levels of denervation in a target region of a patient. 10155j FIG. 14 is a schematic and conceptual illustration of a system 200 including an example generator 214 and an example programmer 224 coupled to a medical imaging system 246 and example catheter 102. In some examples, system 100 may be similar to system 200, and functions described with reference to one or both of generator 214 or programmer 224 may be performed by console 104 of system 1 or another medical device. While various circuitries, algorithms, modules, and functions are described with reference to programmer 224 of FIG. 14, in other examples, generator 214, or another medical device may include features and perform functions described with reference to programmer 224.

Programmer 224 includes a processor 225, a user interface 226, and a memory 228. Memory 228 includes computer-readable instructions that, when executed by processor 225, causes programmer 224 to perform various functions. Processor 225 may include any one or more microprocessors, controllers, digital signal processors (DSPs), application specific integrated circuits (ASICs), field-programmable gate arrays (FPGAs), or equivalent discrete or integrated digital or analog logic circuitry, and the functions attributed to processor 225 herein may be embodied as software, firmware, hardware or any combination thereof.

Memory 228 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 228 may store any suitable information, including patient identification information, and information for generating one or more therapy program with which generator 214 generates and delivers denervation therapy to a patient. For example, memory 228 may store one or more of patient anatomy reconstruction 230, computer model 232, therapy programs 234, stimulation algorithms 236, and operating instructions in separate memories within memory 228 or separate areas within memory 228.

Each therapy program 234 defines a particular program of therapy in terms of respective values for denervation stimulation parameters, such as the electrodes with which the stimulus is delivered to a patient, electrode polarity (if applicable), duty cycle, current or voltage amplitude, and/or frequency, or appropriate non-electrical parameters in examples in which the denervation stimulus includes non-electrical stimulus. Memory 228 may also store operating instructions with which processor 225 controls the operation of programmer 224, and may include instructions for measuring the impedance of electrodes and/or determining placement and orientation of electrodes along the blood vessel.

Generator 214 is configured to receive one or more therapy programs 234 from programmer 224, and apply the denervation therapy parameter values specified by the received one or more therapy programs 234, such as amplitude, duty cycle, and frequency, to generate a denervation stimulus. For example, generator 214 may control stimulation circuitry 238 to generate a denervation stimulation signal according to a particular therapy program, and deliver the denervation stimulation signal via catheter 102. Stimulation circuitry 238 may be electrically coupled to the one or more conductors of catheter 102 using any suitable technique. For example, generator 214 may include switching circuitry configured to switch the stimulation generated by stimulation circuitry 238 across different electrodes or stimulation generator 214 may include multiple energy sources to drive more than one electrode at one time.

In some examples, generator 214 may include sensing circuitry 240 coupled to catheter 102, for example, to receive electrical measurements, feedback, or signals, for example, impedance, which a processor of generator 214 may automatically control the delivery of a denervation stimulation signal via catheter 102.

In some examples, system 200 may include one or both of drive circuitry 241 or drive unit 248 ultimately coupled to therapy delivery device to control one or more of movement, location, or orientation of catheter 102 along the blood vessel in which catheter 102 is disposed. For example, drive unit 248 may include a stepper motor, a servo motor, or suitable motor, or magnetic rail, or any other suitable mechanism for advancing, retracting, rotating, and repositioning catheter 102 along the blood vessel. Drive circuitry 241 may control operation of drive unit 248, for example, by amplifying or sending control signals from processor 225 to drive unit 248. In some examples, drive circuitry 241 may receive feedback signals from drive unit 248 indicative of a current location or orientation of catheter 102, and freedom of or resistance to movement of catheter 102, and may send such feedback signals to processor 225 for ultimately controlling the movement and position of catheter 102.

A user, either a clinician or patient, may interact with processor 225 through user interface 226. User interface 226 may include a display, such as a liquid crystal display (LCD), light-emitting diode (LED) display, or other screen, to present information related to stimulation therapy, and buttons or a pad to provide input to programmer 224. In examples in which user interface 226 requires a 3D environment, the user interface may support 3D environments such as a holographic display, a stereoscopic display, an autostereoscopic display, a head-mounted 3D display, or any other display that is capable of presenting a 3D image to the user. Buttons of user interface 226 may include an on/off switch, plus and minus buttons to zoom in or out or navigate through options, a select button to pick or store an input, and pointing device, e.g. a mouse, trackball, or stylus. Other input devices may be a wheel to scroll through options or a touch pad to move a pointing device on the display. In some examples, the display may be a touch screen that enables the user to select options directly from the display screen.

In some examples, programmer 224 may include a telemetry module that may support wired or wireless communication between programmer 224 and generator 214 or another computing device under the control of processor 225. A clinician or another user may interact with programmer 224 to generate and/or select therapy programs 234 for delivery via catheter 102. In some examples, programmer 224 may allow a clinician to define target volumes of influence, and generate appropriate therapy delivery parameter values to achieve the desired volumes of influence. Programmer 224 may be used to present anatomical regions to the clinician via user interface 226, select therapy programs 234, generate new therapy programs 234 by manipulating computer model 232 or estimated volumes of influence presented on a GUI on user interface 226, and communicate the selected therapy programs 234 to the generator 214.

Programmer 224 may include a power source for delivering operating power to the components of programmer 224. The power source may include at least one battery and a power generation circuit to produce the operating power. In some examples, the battery may be rechargeable to allow extended operation. Recharging may be accomplished through proximal inductive interaction, or electrical contact with circuitry of a base or recharging station. In other examples, primary batteries (e.g., nickel cadmium or lithium ion batteries) may be used. In addition, programmer 224 may be directly coupled to an alternating current source, such would be the case with some computing devices, such as personal computers. The power source may include circuitry to monitor power remaining within a battery. In this manner, user interface 226 may provide a current battery level indicator or low battery level indicator when the battery needs to be replaced or recharged. In some cases, the power source may be capable of estimating the remaining time of operation using the current battery.

In some examples, programmer 224 may be communicatively coupled to medical imaging system 246, or may otherwise receive one or more medical images of a patient from medical imaging system 246. Medical imaging system 246 may be configured to generate a medical image of a region of a patient that includes a target nerve (e.g., intended to be denervated) and, in some cases, a corresponding blood vessel. The corresponding blood vessel may be, for example, an artery or another blood vessel through which the target nerve may be accessed by a therapy delivery device. One or more medical images generated by medical imaging system 246 may be stored by programmer 224 in memory 228, or otherwise used by processor 225, to generate patient anatomy digital reconstruction 230. The medical image can be any medical image that provides sufficient resolution for identifying the tissue regions to avoid (for example, particular muscles, lymph nodes, other blood vessels veins/arteries, the kidney itself, the digestive tract, or other anatomical features or tissue).

In some cases, memory 228 of programmer 224 or another device (e.g., a remote device) may store a plurality of medical images of a patient, which can be, for example, a plurality of medical images of the same or nearly the same region of the patient. In some cases, if there has been a relatively large gap of time between denervation therapy sessions (e.g., on the order of weeks, months, or even years), a clinician may elect to use medical imaging system 246 to generate one or more updated medical images of the patient or otherwise obtain updated medical images of the patient, and update the one or more therapy programs used by generator 214 based on the one or more updated medical images. In some examples, the plurality of medical images may include any suitable available medical images of the patient region, for example, images obtained of the patient region obtained for a therapy other than denervation therapy. There may be changes to a particular patient's anatomy and/or tissue characteristics over time, such as due to weight gain, weight loss, or the like.

In some examples, medical image system 246 includes at least one of a fluoroscopy system, a computer aided tomography (CAT) scan system, a magnetic resonance imaging (MRI) system, a positron emission tomography (PET) scan system, an electrical impedance tomography (EIT) system, an ultrasound system, or an optical imaging system. Processor 225 may be configured to develop computer model 232 based on patient anatomy reconstruction 230. In some examples, computer model 232 includes a finite element model. In some examples, digital reconstruction 230 includes a three-dimensional (3D) reconstruction. Processor 225 may use one or both of digital reconstruction 230 or computer model 232 to determine an estimated volume of influence of denervation therapy, and determine one or more therapy programs 234 based on the estimated volume of influence, as described with reference to FIGS. 15 to 18. Processor 225 may further also be used to deliver and monitor delivery of denervation therapy by generator 214 based on therapy programs 234, as described with reference to FIGS. 15 to 18.

Figure 15:
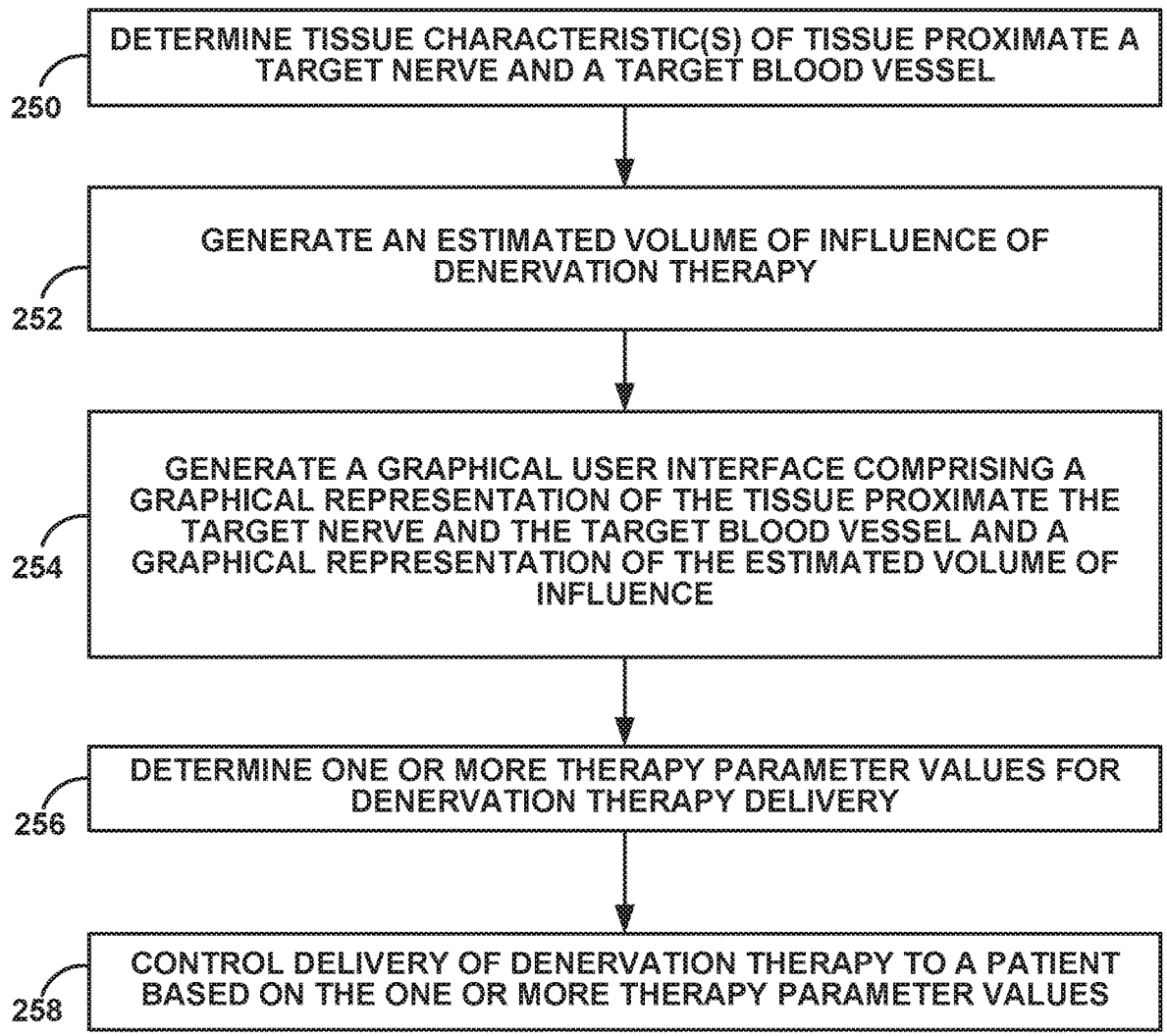
FIG. 15 is a flow diagram illustrating an example technique for delivering denervation therapy.

FIG. 15 is a flow diagram illustrating an example technique for delivering denervation therapy. The example techniques of FIGS. 15 to 18 are described with reference to the example systems 100 and 200 of FIGS. 1 and 14. However, example techniques of FIGS. 15 to 18 may be performed using any suitable systems or devices. In some examples, the example technique of FIG. 15 includes determining, by processor 225, one or more tissue characteristics of tissue proximate a target nerve and a blood vessel (250). The tissue characteristics may include, but are not limited to, one or more of electrical impedance, thermal conductivity, acoustic impedance, chemical diffusivity, optical transmittivity, or density of tissue. In some examples, processor 225 may determine the tissue characteristics by at least generating a computer model 232 based on digital reconstruction 230 including the target nerve and blood vessel, as described with reference to FIG. 16.

Processor 225 may generate, based on the one or more tissue characteristics, at least one estimated volume of influence of denervation therapy delivered according to one or more respective therapy programs via catheter 102 disposed within the blood vessel (252). For example, based on the thermal and electrical conductivity associated with different tissue types identified from computer model 232 of the region of the patient, processor 225 may determine the volumetric reach to which energy or denervation stimulation may be electrically or thermally conducted from electrodes (or generally from a location and orientation of a therapy delivery element of catheter 102). As an example, processor 225 may determine the estimated propagation of RF signals having predetermined frequencies and amplitudes, and the estimate propagation of thermal waves, based on tissue properties such as conductivities and densities. As another example, based on chemical diffusivity of tissue indicated from computer model 232 of the region of the patient, processor 225 may determine the volumetric reach of chemical stimulation resulting from delivery of a chemical agent delivered by catheter 102. In some examples, tissue at or adjacent a target treatment site may be modified, for example, by injecting electrically conductive material or electrically insulative material. In some such examples, processor 225 may determine changes in conductivity or other properties of tissue resulting from tissue modification, and computer model 232 may include a representation of modified tissue regions. By modeling different amounts (e.g., volumes) and locations for injection of electrically conductive or electrically insulative material, and determining the resulting volumes of influence of denervation stimulation, processor 225 may determine whether the use of the electrically conductive material or electrically insulative material would be beneficial to a particular patient and, if so, determine the volume and/or one or more locations for injecting the electrically conductive material or electrically insulative material. For example, processor 225 may determine one or more locations for injecting the electrically conductive material or electrically insulative material and respective amounts of the electrically conductive material or electrically insulative material to be injected at respective locations for targeting a given nerve or nerve bundle, while avoiding non-target sites. In addition or instead, in some examples, processor 225 may determine one or more locations for injecting the electrically conductive material or electrically insulative material and respective amounts of the electrically conductive material or electrically insulative material to be injected at respective locations for achieving efficient (in terms of power usage) denervation of a given nerve or nerve bundle, while avoiding non-target sites.

In some examples, computer model 232 may account for blood flow rates in one or more blood vessels in a region of the patient. For example, a blood flow rate in a blood vessel, for example, a renal artery, may affect the volume of influence resulting from delivery of a stimulus by catheter 102. For example, a higher blood flow rate may cause relatively faster thermal dissipation, leading to a smaller volume of influence for a given denervation stimulus than a volume of influence associated with a lower blood flow rate. In some examples, computer model 232 may include blood flow rates at or near a target tissue site, which may help increase the efficacy, efficiency, or both, of denervation therapy delivery by a catheter 102 compared to denervation therapy delivered in an ad hoc manner, without the aid of computer model 232. The patient-specific anatomy can include, for example, the locations and relative arrangement of different anatomical structures of the patient (e.g., organs, blood vessels, target tissue sites, and the like), and the size of one or more blood vessels, which may correspond to a blood flow rate through the vessel, and, therefore, thermal and/or electrical conductivity of the blood vessel.

Processor 225 may use any suitable technique to determine the estimated volume of influence, including, but not limited to, a finite element model or another algorithm that numerically represents how different stimuli affect different types of tissue. Regardless of whether the stimulus is an electrical, thermal, chemical, optical, or other type of stimulus, the estimated volume of influence may be indicative of the extent of denervation stimulus and may be indicative of viability of nerve and non-nerve tissue subjected to the denervation stimulus. For example, processor 225 may determine that no lesions may be formed in tissue outside the estimated volume of influence, while lesions may be formed within the estimated volume of influence. Thus, in some examples, the estimated volume of influence includes a lesion, for example, a denervating lesion.

In some examples, processor 225 may determine two or more estimated volumes of influence based on respective therapy programs. For example, processor 225 may generate a first estimated volume of influence of a first denervation therapy delivered by catheter 102 according to a first therapy program of therapy programs 234, and determine a second estimated volume of influence of a second denervation therapy delivered by catheter 102 according to a second therapy program of therapy programs 234. The second therapy program includes at least one therapy parameter value different from a respective therapy parameter value of the first therapy program.

In some examples, processor 225 may determine multiple therapy programs that each provides efficacious results for a particular patient, e.g., due to similar targeting of the renal nerve or other nerve or target tissue site of interest by denervation stimuli. However, the result of the delivery of the denervation therapy according to the different therapy programs may differ from each other in one or more ways. For example, some therapy programs may define denervation stimuli that require more power to generate than one or more other therapy programs, such that some therapy programs may be more efficient (for example, in terms of power usage) than others. As another example, some therapy programs may result in lesioning of more non-target tissue than one or more other therapy programs. Thus, processor 225 may select a therapy program not only based on the estimated lesioning of the target tissue site, but also based one or more other factors, such as the power consumed during a therapy session, the effect on a non-target tissue site, and the like. In some examples, processor 225 may order a list of therapy programs based on one or more of these other factors (e.g., ascending or descending order based on power consumption, non-target tissue site volume affected by the therapy, or the like), and present the ordered list of therapy programs to a user via a display of user interface 226. Processor 225 may then select the one or more therapy programs for controlling delivery of the therapy to a patient in response to a user input, or automatically based on the top one or more predetermined number of therapy programs in the ordered list.

In some examples, processor 225 may generate a plurality of therapy programs (which differ from each other by at least one therapy parameter value of a given therapy parameter), and determine a plurality of volumes of influence, each volume of influence of the plurality of volumes of influence being associated with a respective therapy program of the plurality of therapy programs. Processor 225 may determine a volume of influence of the plurality of volumes of influence, for example, at least one volume of influence that extends to a tissue of interest, while avoiding non-target sites, for example, predetermined adverse effect sites. Based on the at least one volume of influence, processor 225 may select a therapy program of the plurality of therapy programs for delivering the denervation therapy to the patient. Processor 225 may control generator 214 to generate and deliver denervation therapy according to the therapy delivery parameters defined by the selected therapy program, generating the at least one volume of influence at the target tissue site, such that the at least one volume of influence does not impact or extend into a non-target tissue site.

In some examples, processor 225 may generate a plurality of therapy programs (which differ from each other by at least a location of volume of influence along a vessel). For example, processor 225 may generate a plurality of therapy programs delivered at a plurality of locations along the vessel, for example, six, nine, twelve, or any suitable number of locations along the length of the vessel. Processor 225 may determine a plurality of volumes of influence, each volume of influence of the plurality of volumes of influence associated with a respective location of the locations along the vessel. In some examples, two or more volumes of influence along the vessel may overlap in volume. In some examples, processor 225 may select a therapy program that achieves a relatively simple pattern of therapeutic influence, for example, ablation, along the vessel. For example, the simple pattern may be the most efficient with respect to power usage or duration of a therapy session, or the easiest for a clinician to deliver, or may result in relatively lowest adverse effects along the vessel in non-target tissue sites along the vessel, or otherwise result in a given pattern of therapy delivery along the vessel. In some examples, processor 225 may select a therapy program that generates a pattern of volumes of influences along the vessel for a given therapy delivery device, for example, a given type or configuration or orientation of catheter or electrodes along the therapy delivery device. In some examples, the given therapy delivery device may include a catheter defining a spiral or helical portion, and three, four, or more electrodes or any suitable therapy delivery elements simultaneously delivering therapy along the spiral or helical portion.

In some examples, processor 225 may select a therapy program generating different volumes of influence, for example, extending to different geometric volumes, at different locations along the vessel. The particular volumes of influence at specific locations may correspond to, for example, the location of the target tissue site (e.g., a renal nerve) relative to the therapy delivery device. In some examples, the therapy program may generate a smaller volume of influence at one or more locations along the vessel, and a larger volume of influence along other locations along the vessel. In some examples, the volumes of influence may progressively increase in volume, or progressively decrease in volume, along the vessel.

In some examples, processor 225 may select a plurality of therapy programs, each therapy program of the plurality of therapy programs associated with a location of the different locations along the vessel. Different therapy programs of the plurality of therapy programs may differ in one or more therapy parameters at different locations. In some examples, the respective magnitudes of therapy parameters of respective therapy programs may progressively increase, or progressively decrease, along the vessel.

In some examples, processor 225 generates a GUI (for example, GUI 290 or GUI 320 described with reference to FIGS. 19 and 20) (254), which may include a graphical representation of the tissue proximate the target nerve and the blood vessel and a graphical representation of the estimated volume of influence. This GUI may provide a clinician with the information to relatively quickly ascertain the therapeutic effects of a particular therapy program on a particular patient in ways that existing renal denervation therapy programming that do not provide such patient-specific modeling may not allow.

In addition to or instead of generating the GUI, processor 225 may determine, based on the estimated volume of influence, one or more therapy parameter values for efficacious denervation therapy delivery (256). For example, processor 225 may select one or more of the modeled therapy programs 234 based on the resulting estimated volume of influence (252). The therapy parameter values may include, for example, at least one of an electrical signal parameter, a thermal signal parameter, an ultrasound signal parameter, a microwave signal parameter, or a chemical dosage parameter. In some examples, the therapy parameter values can include, for example, respective locations within the patient for the delivery of a denervation stimulus. Processor 225 may select the one or more therapy parameter values using any suitable criterion or criteria. For example, in some cases, processor 225 determines the one or more therapy parameter values by at least selecting the one or more therapy parameter values (or therapy programs) determined to result in lesioning of the target nerve and avoiding lesioning of a predetermined adverse-effect region. In other examples, processor 225 determines the one or more therapy parameter values by at least selecting the one or more therapy parameter values (or therapy programs) determined to avoid lesioning of a predetermined adverse-effect region, without necessarily resulting in estimated lesioning of the target nerve.

In examples in which processor 225 generates estimated volumes of influence, processor 225 determines the one or more therapy parameter values for denervation therapy delivery by at least selecting a subset (e.g., one or more) of the plurality of modeled therapy programs. For example, in the example above in which processor 225 generates estimated volumes of influence for each of a first therapy program and the second therapy program based on the respective first and second estimated volumes of influence, processor 225 may select the therapy program associated with the volume of influence that encompasses a denervation target nerve, and/or results in a volume of influence that avoids lesioning of a predetermined adverse-effect region (for example, a tissue or organ in which lesioning is not sought).

In some examples, processor 225 may generate a GUI that orders the therapy programs 234 based on determined efficacy (e.g., resulting in lesioning of a target nerve and/or avoiding lesioning of an adverse-effect region, or a clinician may otherwise select one of therapy programs 234. For example, processor 225 may associate each stored therapy program 234 with a numerical score based on the associated estimated volumes of influence, the score indicating, for example, the amount of overlap of the estimated volume of influence with the target nerve and/or amount of overlap with an adverse-effect region. Processor 225 may then order the therapy programs 234 in ascending or descending order based on scores. A clinician may then quickly review the ordered list of therapy programs to determine which one or more therapy programs should be used to program generator 214.

In some examples, processor 225 may controls generator 214 to generate and deliver denervation therapy to a patient based on the determined one or more therapy parameter values of therapy programs 234 (258). For example, processor 225 may transmit one or more selected therapy programs 234 to generator 214 via wired or wireless communication, or directly controls stimulation circuitry 238 to generate and deliver the denervation therapy based on a selected therapy program 234.

In some examples, the example technique further includes generating, by processor 225 and based on the estimated volume of influence, an indexed location of catheter 102 within the patient, and associating the indexed location with a particular therapy program. For example, the indexed location may be a location along the blood vessel (or alone a shaft of catheter 102), and the indexed location may be a location of a therapy delivery element (for example, electrodes) of catheter 102 relative to the blood vessel or another anatomical landmark or landmark on catheter 102. The indexed locations may be used to determine the extent to which catheter 102 has advanced within the blood vessel or otherwise the proximity of one or more therapy delivery elements (for example, electrodes) of catheter 102. In some examples, drive unit 248 may advance or retract catheter 102 along the blood vessel by monitoring the index locations, for example, index locations on catheter 102 that may be ascertainable external to the body vessel.

Any suitable technique may be used by a processor of drive unit 248 to control the position of catheter 102. For example, drive unit 248 may include an optical unit that monitors visible markers on catheter 102 to determine the relative position of catheter 102 relative to an entry point into the patient. As another example, catheter 102 may include magnetic markers, and drive unit 248 may determine the relative position of catheter 102 (e.g., relative to programmer 224) using the magnetic markers, e.g., the magnitude of a magnetic field generated by the magnetic markers and sensed by a sensor of drive unit 248. In some examples, catheter 102 may include radiopaque or x-ray markers detectable under fluoroscopy, which the clinician or drive unit 248 may align with predetermined registration markers overlaid on a display of the fluoroscopic or other medical image. The radiopaque markers overlaid on a displayed medical image may enable the clinician to manually assess positioning of catheter 102.

In some examples, processor 225 may generate a GUI that includes an image, such a fluoroscopic image of the region of the patient, and may overlay markers on the image to show a clinician where the indexed locations are located relative to patient anatomy. Processor 225 may overlay one marker at a time to help guide the clinician to a next location for delivery of a denervation stimulus, or may overlay a plurality of markers at a time. For example, the clinician may compare the overlaid markers with markers indicative of the indexed locations, for example, radiopaque markers on catheter 102. A clinician may use this information to manually guide catheter 102 to different locations within the patient during a medical procedure. In other examples, processor 225 may communicate with a fluoroscopy imaging system or another imaging system, which may then overlay the one or more markers on a medical image of the patient similar to the foregoing example.

Figure 16:
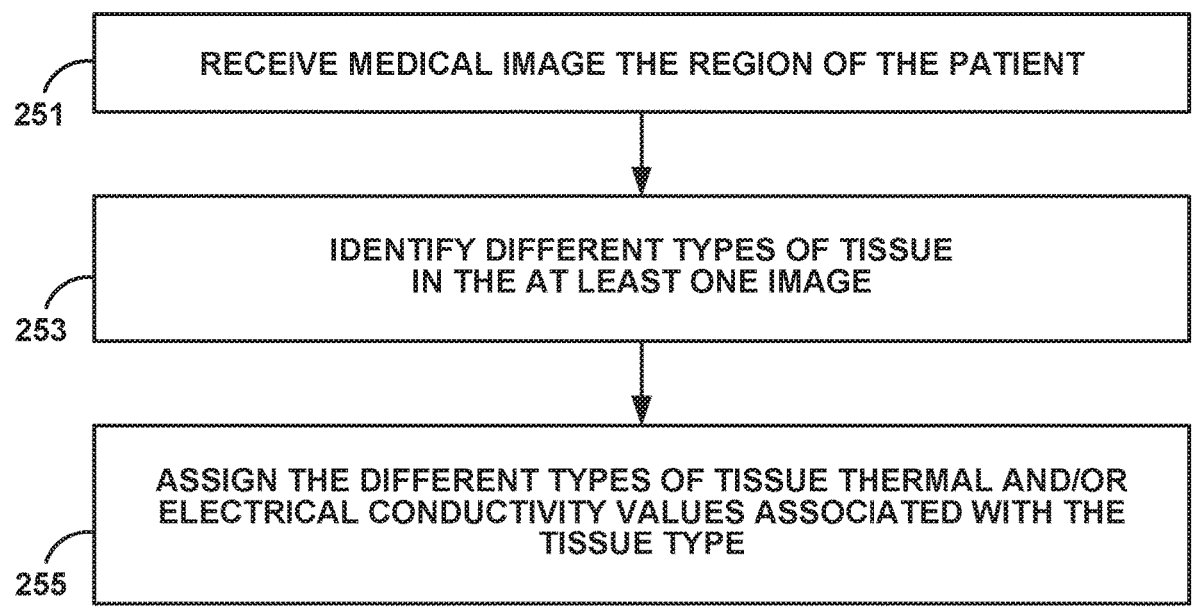
FIG. 16 is a flow diagram illustrating an example technique for generating a computer model of a region of the patient.

As discussed above, in some examples, processor 225 generates a computer model of a region of a patient, where the computer model defines a spatial representation of tissue, including respective tissue characteristics (e.g., thermal conductivity, electrical conductivity, density, and/or the like), in the region. Processor 225 may generate the computer model using any suitable technique. FIG. 16 is a flow diagram illustrating an example technique for generating a computer model of a region of the patient.

In the example of FIG. 16, processor 225 receives at least one medical image of the region the patient from medical imaging system 246 (151). Any suitable imaging modality may be used for the medical image, examples of which are described above. Based on the at least one image, processor 225 may identify different types of tissue in the at least one image (153). Example tissue types include, but are not limited to, bones, tendons, muscle, fat, lymph nodes, blood vessels, and/or organs. As another example, example tissue types may merely be based on the tissue characteristics, such as, but not limited to, the thermal or electrical conductivity of the tissue, the density of the tissue, the chemical diffusivity of the tissue, sonic or ultrasonic parameters, for example, speed of sound or attenuation, or the like or any combination thereof.

For example, processor 225 may identify predetermined tissue types in the at least one image based on location, size, or one or more visual characteristics of the image (e.g., depth of the color of the image), or coordinating with expected densities of different tissue types. As another example, processor 225 may receive user input via user interface 226 (FIG. 14) that identifies different tissue types in the image. For example, a user may provide input outlining different sub-regions of tissue types and identifies the tissue types, such as by assigning the different sub-regions a particular tissue type. Processor 225, however, may also do this automatically in some examples, such as by using image processing techniques, e.g., edge detection, to find boundaries between different tissue types. By identifying the different types of tissue in the at least one image, processor 225 may generate a map of the region of the patient, which indicates the relative location and types of tissue proximate a target nerve and associated blood vessel.

Processor 225 may assign the different types of tissue corresponding tissue characteristics associated with known tissue types (155). For example, processor 225 may assign different identified tissue types within the medical image respective thermal and/or electrical conductivity values or chemical diffusivity values associated with the respective tissue types. In some examples, one or more of thermal or electrical conductivities and tissue densities for different tissue types may be generic to patients, or at least to some classes of patients (e.g., tissue characteristics of newborns may be similar to each other, while tissue characteristics of geriatric patients may be similar to each other). Processor 225 may associate different tissue types with respective tissue characteristics in memory 228 (FIG. 14) of programmer 224 or a memory of another device.

Processor 225 may use, in addition to, or instead of, the at least one image, electrical maps of the patient region, for example, an impedance map determined by a plurality of electrodes introduced into the region of the patient to generate the computer model. In some examples, the clinician may designate the tissue type, and processor 225 may assign the tissue type identified by the clinician with respective tissue characteristics (for example, thermal and electrical conductivities and density). In this way, by combining tissue characteristics with spatial relationships of different tissue types identified in the at least one image, processor 225 may generate computer model 232 representing tissue characteristics at different sites within the patient region in the image. The computer model 232 may be, for example, a digital reconstruction of the region of the patient.

In some examples, processor 225 may process multiple images to generate a 2D or 3D computer model 232. The electrical maps and/or images may be registered to each other using any suitable, such as by aligning anatomical landmarks (e.g., boney landmarks) visible in the images and/or maps.

Figure 17:
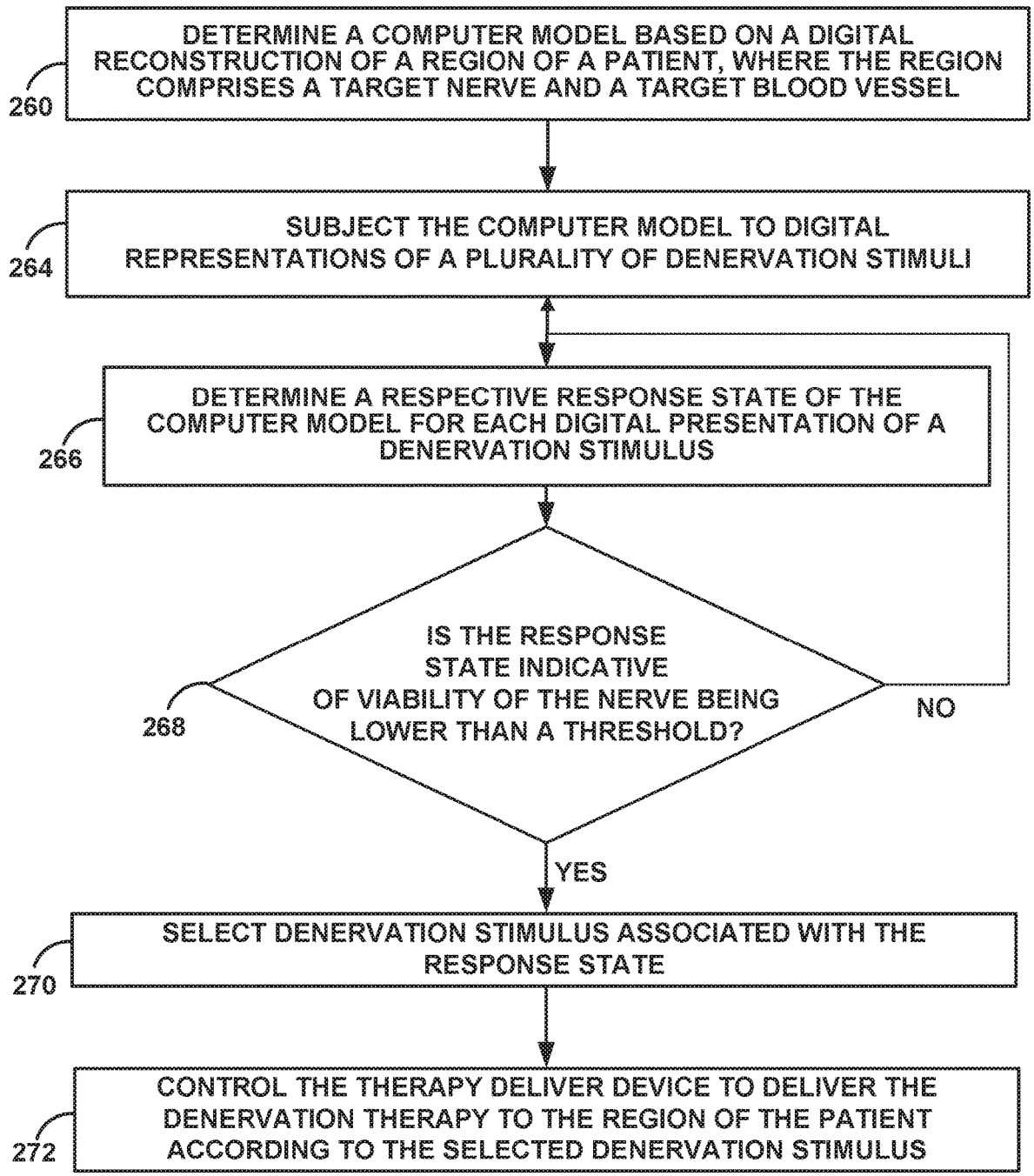
FIG. 17 is a flow diagram illustrating an example technique for delivering denervation therapy.

FIG. 17 is a flow diagram illustrating another example technique for delivering denervation therapy. The technique shown in FIG. 17 may be a more specific example of the technique of FIG. 15. In some examples of the technique shown in FIG. 17, processor 225 determines a computer model 232 based on a digital reconstruction 230 of a region of a patient (260). The region includes a target nerve and a blood vessel. Computer model 232 defines a spatial representation of one or more tissue characteristics in the region. Processor 225 can determine computer model 232 by generating computer model 232, e.g., using the technique described with respect to FIG. 16, or by retrieving an already-generated computer model 232 from memory 228 of programmer 224 or a memory of another device.

Processor 225 subjects computer model 232 to digital representations of a plurality of denervation stimuli (264). For each of the digital representations of a denervation stimulus, processor 225 simulates the delivery of the respective denervation stimulus the digital reconstruction of tissue of the patient by (a digital representation of) catheter 102 in a respective pre-determined orientation and at a respective predetermined location along the blood vessel. Processor 225 determines a respective response state of computer model 232 to each of the digital representations of a denervation stimulus (266). For example, processor 225 may generate the estimated volume of influence based on the magnitude, orientation, and direction of the denervation stimulus, and based on the tissue properties (as represented in computer model 232) of tissue adjacent the target nerve and the blood vessel. The response state may indicate how far the denervating effects of the denervation stimulus are expected to propagate from the catheter 102 within the patient, given the tissue characteristics of tissue proximate the therapy delivery elements of catheter 102.

In the technique shown in FIG. 17, processor 225 generates an estimated volume of influence expected to result from delivery of denervation catheter 102 according to a particular therapy program by subjecting computer model 232 to the digital representations of the plurality of denervation stimuli and determining the response state of the computer model 232 to the respective denervation stimulus.

Processor 225 may select the denervation stimulus for therapy delivery to the patient based on the determined response states. For example, processor 225 may determine a viability of the target nerve based on the response state, and may compare the viability with a threshold (268). In some examples, processor 225 may determine viability based on temperature the target nerve or adjacent tissue is expected to attain, and the time period for which the target nerve or adjacent tissue is expected to maintain the temperature. For example, a lower time duration may be sufficient to affect viability if the expected temperature is relatively higher. If the viability of the nerve is less than the threshold, then the response state may be indicative of denervation of the target nerve (because the viability of the nerve reduced to below the threshold). In some such examples, processor 225 may select the at least one denervation stimulus in response to determining that the respective response state associated with the selected at least one denervation stimulus is indicative of viability of the nerve being lower than a threshold (270). In such examples, processor 225 may store the therapy program used to generate the denervation stimulus in therapy programs 234 as an efficacious therapy program, or by storing the therapy program as a new therapy program added to therapy programs 234. In some examples, processor 225 may associate that therapy program with the particular target nerve, so that processor 225 or another device may select the therapy program if that target nerve is to be denervated.

In some examples, the region of the patient includes at least one non-target non-nerve tissue. In some such examples, in addition to or instead of non-viability or low viability of the target nerve, a sufficiently high viability of a non-target tissue (for example, non-nerve tissue or organ) may be sought. In some such examples, the respective response state associated with the selected at least one denervation stimulus may be indicative of viability of the non-target non-nerve tissue being greater than the threshold. Thus, in some examples, processor 225 selects the at least one denervation stimulus in response to determining that the respective response state associated with the selected at least one denervation stimulus is indicative of viability of the non-target non-nerve tissue being greater than a threshold. Processor 225 may store the therapy program used to generate the denervation stimulus in therapy programs 234 as an efficacious therapy program, or by storing the therapy program as a new therapy program added to therapy programs 234. In some examples, processor 225 may associate that therapy program with the particular target nerve, so that processor 225 or another device may select the therapy program if that target nerve is to be denervated.

Processor 225 may subsequently use the one or more selected denervation stimuli (or resulting therapy programs) to control delivery denervation therapy by generator 214. For example, processor 225 may control generator 214 to generate and deliver the denervation therapy to the region of the patient via catheter 102 according to the denervation stimuli (or resulting therapy programs) (272).

While a clinician may deploy and manipulate the position, orientation, and initiation of denervation stimulus delivery via catheter 102, in some examples, programmer 224 may control or help the clinician with automated or semi-automated positioning, orienting, or triggering of therapy delivery device.

Figure 18:
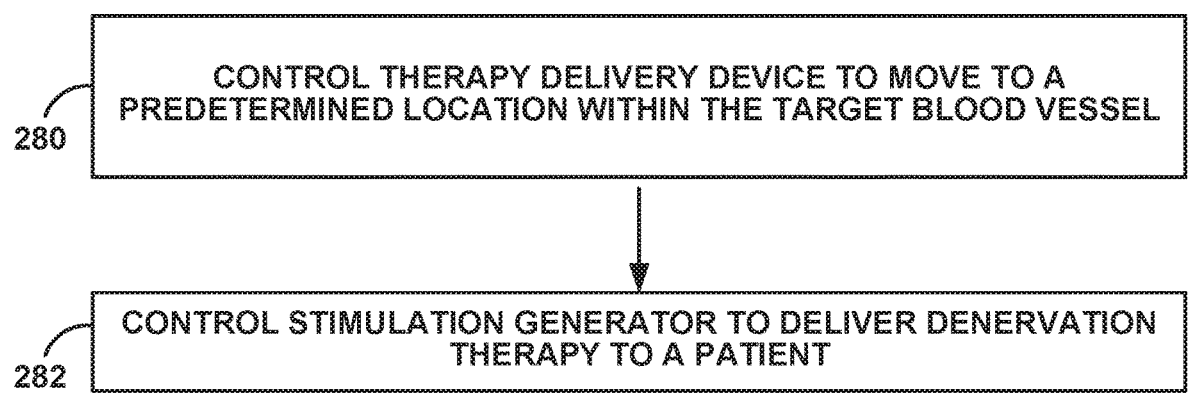
FIG. 18 is a flow diagram illustrating an example technique for delivering denervation therapy.

FIG. 18 is a flow diagram illustrating an example technique for controlling the position of catheter 102 within patient during a medical procedure. Memory 228 of programmer 224 or a memory of another device may store a plurality of indexed locations for catheter 102. The indexed locations may correspond to locations (e.g., relative to some known landmark) at which a therapy delivery element of catheter 102 may be positioned along a length of a blood vessel to provide an even distribution of denervation stimuli. In addition, or instead, the indexed locations may correspond to particular therapy programs selected for the respective location to provide the desirable volumes of influence. As discussed above, because of varying tissue characteristics at different positions along a blood vessel, the denervation therapy parameter values needed to generate a volume of influence that results in the desired therapeutic effect may differ based on the location within the patient. The technique of FIG. 18 may help system 200 provide more efficient and effective denervation therapy in a shorter amount of time by associating known locations with respect therapy programs that have been determined (using computer model 232) to likely result in efficacious therapy delivery to the patient.

In accordance with the technique shown in FIG. 18, processor 225 controls a surgical device to move catheter 102 to a predetermined location within the blood vessel (280). For example, processor 225 may send one or more control signals through drive circuitry 241 or otherwise to drive unit 248, and drive unit 248 may engage catheter 102, and cause catheter 102 to advance, retract, or rotate to assume a predetermined position and orientation along the blood vessel and relative to the target nerve or predetermined non-nerve tissue. Once catheter 102 is at the desired, predetermined location, processor 225 may control generator 214 to deliver denervation therapy to a patient based on the one or more therapy parameter values (282). For example, processor 225 may send generator 214 a control signal that causes generator 214 to deliver the denervation stimulus. As another example, processor 225 may notify a clinician, who may then manually control generator 214 to deliver the denervation stimulus.

As discussed above, in some examples, processor 225 generates a GUI and presents the GUI on a display of user interface 226 of programmer 224. The GUI may present, for example, a graphical representation of a region of a patient that includes a target nerve and, if relevant, a corresponding blood vessel. The corresponding blood vessel can be, for example, a blood vessel through which catheter 102 is introduced to access the target nerve. In some examples, the GUI may only include a graphical representation of a region of a patient that includes a target nerve and, if relevant, a corresponding blood vessel. In other examples, the GUI may include other graphical elements, such as a graphical representation of an estimated volume of influence expected to result from delivery of a denervation stimulus to tissue of the patient via catheter 102. Such a GUI may help a clinician better visualize the denervation therapy and gain a better understanding of the affects that different therapy parameter values, including the location of a therapy delivery element within the patient, may have on the volume of influence.

In some examples, rather than generating a graphical representation of a volume of influence based on a known therapy program as discussed in some examples above, a user may provide input indicating a graphical representation of a desired volume of influence within the GUI, and processor 225, in response, may determine the therapy parameter values that are expected to result in the volume of influence. Processor 225 may then program generator 214 using these therapy parameter values, which may be stored as a therapy program.

Figure 19:
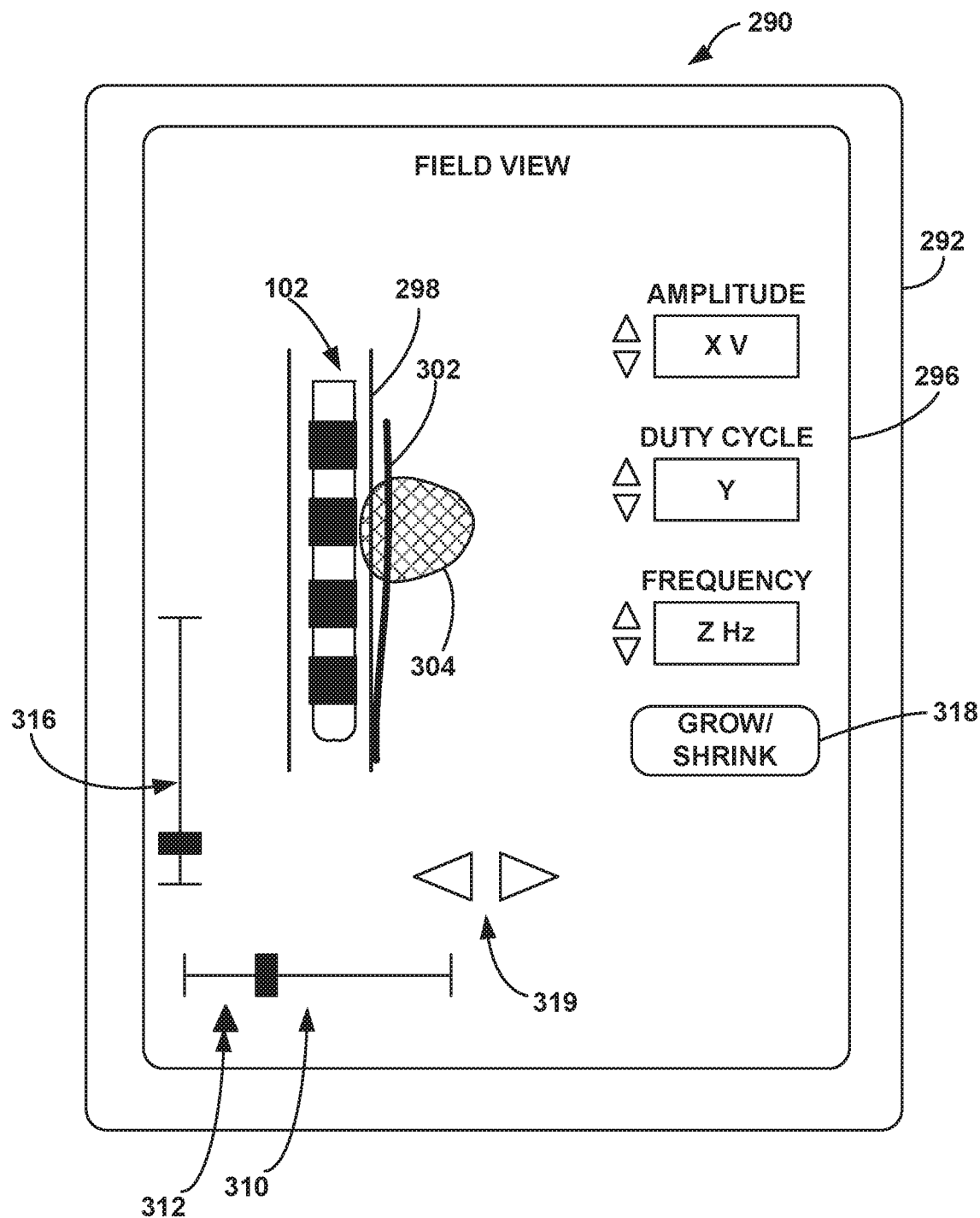
FIG. 19 illustrates a schematic representation of an example graphical user interface (GUI) that may be presented on a display of a user interface of the programmer of FIG. 14.

FIG. 19 illustrates a schematic representation of an example GUI 290 that may be presented on the display of user interface 226 of programmer 224 of FIG. 14. By interacting with GUI 290, a user may generate a graphical representation of an electrical stimulation field, which may be an example of a volume of influence. In some examples, the user may be able to create a stimulation field and direct processor 225 to generate a set of therapy parameter values (e.g., a therapy program) that would best match the stimulation field. In some examples, the user may change the size, shape or position of the stimulation field within GUI 290 using graphical input media such as cursor or stylus control. The generated electrical stimulation field may be utilized as a computer model of a therapy field associated with the generated parameters, for example, the volume of influence associated with electrical denervation stimuli. Thus, the volume of influence may be observed by the clinician using GUI 290, and the clinician may select or modify one or more of therapy programs 234 based on the observed volume of influence.

GUI 290 illustrates a graphical representation of catheter 102, which includes a multi-electrode geometry. In the example of FIG. 19, catheter 102 includes four electrodes at different axial positions, generally arranged in a ring. Each electrode is coupled to a respective electrical conductor within catheter 102. Hence, catheter 102 includes multiple electrical conductors, e.g., wires, cables or the like, that extend from the proximal end of the lead to respective electrodes to electrically couple the electrodes to electrical terminals, for example, those of generator 214.

Each electrode is independently by generator 214 so that stimulation energy can be delivered at different axial and angular positions. In some examples, catheter 102 may include combinations of complex electrode array geometries and simple electrode array geometries. For example, ring electrodes that extend about the entire circumference of the lead may be used in combination with electrodes disposed at different axial and angular positions. Selective activation of the electrodes carried by catheter 102 can produce customizable stimulation fields that may be directed to a particular side of catheter 102 in order to isolate the stimulation field around a target anatomical region.

GUI 290 illustrates a side view of catheter 102, shown to be introduced in a blood vessel 298. Although not shown in FIG. 19 or 20, the graphical representation of catheter 102 may be spiral and in contact with the inner walls of the graphical representation of blood vessel 298. The size and shape of stimulation field 304 may be established based on the generic physical characteristics of tissue, as well as based on known physical characteristics of the electrodes of catheter 102. In other words, stimulation field 304 displayed in GUI 290 may only be an approximation of what the stimulation field would be in the region of the patient including the target nerve. However, in some examples, physical characteristics of the actual anatomical structure of the patient being treated may be used to generate stimulation field 304. This anatomical structure information may be presented to programmer 224 in the form of patient anatomical data generated by an imaging modality, such as CT, MRI, or any other volumetric imaging system and stored within memory 228 (FIG. 14). Processor 225 may generate stimulation field 304 using, for example, tissue impedance models, field propagation models, or the like. In some examples, stimulation field 304 may be a representation of an electrical field, current density, voltage gradient, or neuron activation, applied to a generic human tissue or patient-specific tissue characteristics. In addition, the user may be able to switch between any of these representations when desired.

The user may move stimulation field 304 up or down relative to a longitudinal axis of catheter 102 using vertical scroll bar 316 or some similar control interface. As stimulation field 304 moves up or down in response to the user input, programmer 224 automatically selects appropriate electrode(s) to support the vertical movement of stimulation field 304 within GUI 290. GUI 290 includes arrows 319 or similar input media that permit the user to transition between different rotational views.

In addition, the user may rotate the view shown in GUI 290 using horizontal scroll bar 310 or some similar control device, e.g., to visualize stimulation field 304 relative to other tissue sites not shown in all views. An arrow 312 may be provided next to horizontal scroll bar 310 to indicate the orientation of catheter 102 relative to an anatomical structure.

Movement of stimulation field 304 within GUI 290 using scroll bars 316 or similar input media may permit the user to evaluate different stimulation field positions without the need to manually select electrodes and manually enter parameter values. Instead, processor 225 of programmer 224 automatically selects electrodes and parameter values in response to movement of stimulation field 304 by the user. Although scroll bar 316 is illustrated as examples of input media for movement of stimulation field 304, other types of input media may be used. Examples include up/down arrows or side-to-side arrows, which may be presented on a touch screen or formed by buttons or keys on programmer 224.

As a further alternative to manipulating the stimulation field 304, the user may select stimulation field 304 with a stylus, mouse, or other pointing device and drag the field upward, downward, or rotationally. In some examples, a mouse or other pointing device may support left or right click functionality to perform different operations relative to stimulation field 304. With a stylus, a first click on stimulation field 304 may initiate movement, dragging with the stylus directs movement relative to the schematic illustration of catheter 102 in GUI 290, and a second click may terminate movement. In each case, processor 225 of programmer 224 responds to the specified movement by automatically adjusting the electrode combination and the stimulation parameters to approximate the characteristics of stimulation field 304 presented by GUI 290. As the stimulation parameter values change, the size and shape of stimulation field 304 presented on the display change. Similarly, as the electrode combination changes in terms of polarity or electrode selection, the size, shape or direction of stimulation field 304 presented on the display changes.

In some examples, processor 225 of programmer 224 may utilize stimulation templates and select the best fitting stimulation template set to a newly modified stimulation field 304 in order to generate therapy parameter values for achieving stimulation field 304. A stimulation template is a predetermined volumetric stimulation field that processor 225 of programmer 224 may substantially match to a desired stimulation field 304 from the user. An algorithm for generating stimulation parameter values that fit the user defined stimulation field may be less computationally intensive for processor 225 compared to an algorithm that references multiple equations or lookup tables to generate the stimulation parameters. The stimulation template may be a representation of an electrical field or other electrical stimulation related characteristic, e.g., current density, voltage gradient, or neuron activation, applied to a generic human tissue. For stored stimulation templates, processor 225 may adjust the RF energy to alter the size of the stimulation template to cover the desired stimulation field 304 from the user.

Processor 225 of programmer 224 may limit the rate of movement of stimulation field 304 within GUI 290. In other words, stimulation field 304 may only be moved a certain number of steps per second within GUI 290, or any other user interface that allows the user to drag the stimulation field. This rate movement limit may prevent unnecessary calculations or ensure patient comfort in real-time programming examples.

In addition to moving stimulation field 304, GUI 290 may permit the user to perform one or more operations that result in reconfiguration of stimulation field 304. For example, the user may click on a border, i.e., an outer perimeter, of stimulation field 304, and drag it inward or outward to resize the stimulation field. Resizing by enlarging or shrinking stimulation field 304 in GUI 290 may result in an increase or decrease in RF energy, and, therefore, changes to the parameter values of a therapy program used to generate stimulation field 304. In some examples, enlarging or shrinking stimulation field 304 also may result in selection or de-selection of electrodes included in the existing electrode combination. In either case, processor 225 of programmer 224 adjusts the electrode combination and/or parameter values in response to the enlargement or shrinkage of stimulation field 304 by the user.

When a user clicks on stimulation field 304 border and drags it, the entire stimulation field may be expanded in two dimensions in equal proportions. Alternatively, stimulation field 304 may expand only in the direction in which the user drags the stimulation field. For example, horizontal dragging of the field perimeter to enlarge stimulation field 304 may result in overall enlargement of the cross-sectional seize of stimulation field 304, keeping the vertical to horizontal aspect ratio constant. Alternatively, horizontal dragging may result only in horizontal expansion, leaving the vertical dimension constant. The application of a constant or varying aspect ratio may be specified by a user as a user preference. Alternatively, programmer 224 may provide different aspect ratio modes on a selective basis for expansion and shrinkage of stimulation field 304.

To enlarge or shrink stimulation field 304, the user may simply click on the stimulation field border within GUI 290. Alternatively, the user may click on a grow/shrink button 318 as shown in FIG. 19, and then click on the border of stimulation field 304 to drag it inward or outward and thereby adjust the size of the stimulation field. In response, processor 225 of programmer 224 may automatically reconfigure the selected electrode(s) and/or stimulation parameter values to approximate the resized stimulation field. In this way, a user may generate a volume of influence by directly manipulating the stimulation field 304. In each case, the user changes stimulation field 304 by simply changing the representation of the stimulation field 304 presented on GUI 290, thereby avoiding the need to manually select electrodes and parameter values.

A user may manipulate the size, shape, and/or location of stimulation field 304 (or another type of volume of influence in other examples) in order to, for example, better target a target nerve and/or to avoid an adverse-effect region. Thus, although not shown in FIG. 19, GUI 290 may include a graphical representation of the target nerve, an adverse-effect region, and/or other tissue sites of interest, or may at least include a medical image of the region of the patient overlaid with the graphical representation of catheter 102 and stimulation field 304. In some cases, a target nerve may not be visible in a medical image. In these examples, a graphical representation of an adverse-effect region, and/or other tissue sites of interest may still be useful information to present, as it would still guide a user to select denervation therapy parameter values that may avoid the adverse-effect region.

After selecting a desirable stimulation field 304, processor 225 of programmer 224 may determine the one or more therapy parameter values that are expected to result in the desirable stimulation field 304, e.g., based on computer model 232. Processor 225 may, in some examples, control generator 214 or another medical device to deliver denervation therapy to the region of the patient in accordance with the one or more therapy parameter values.

Figure 20:
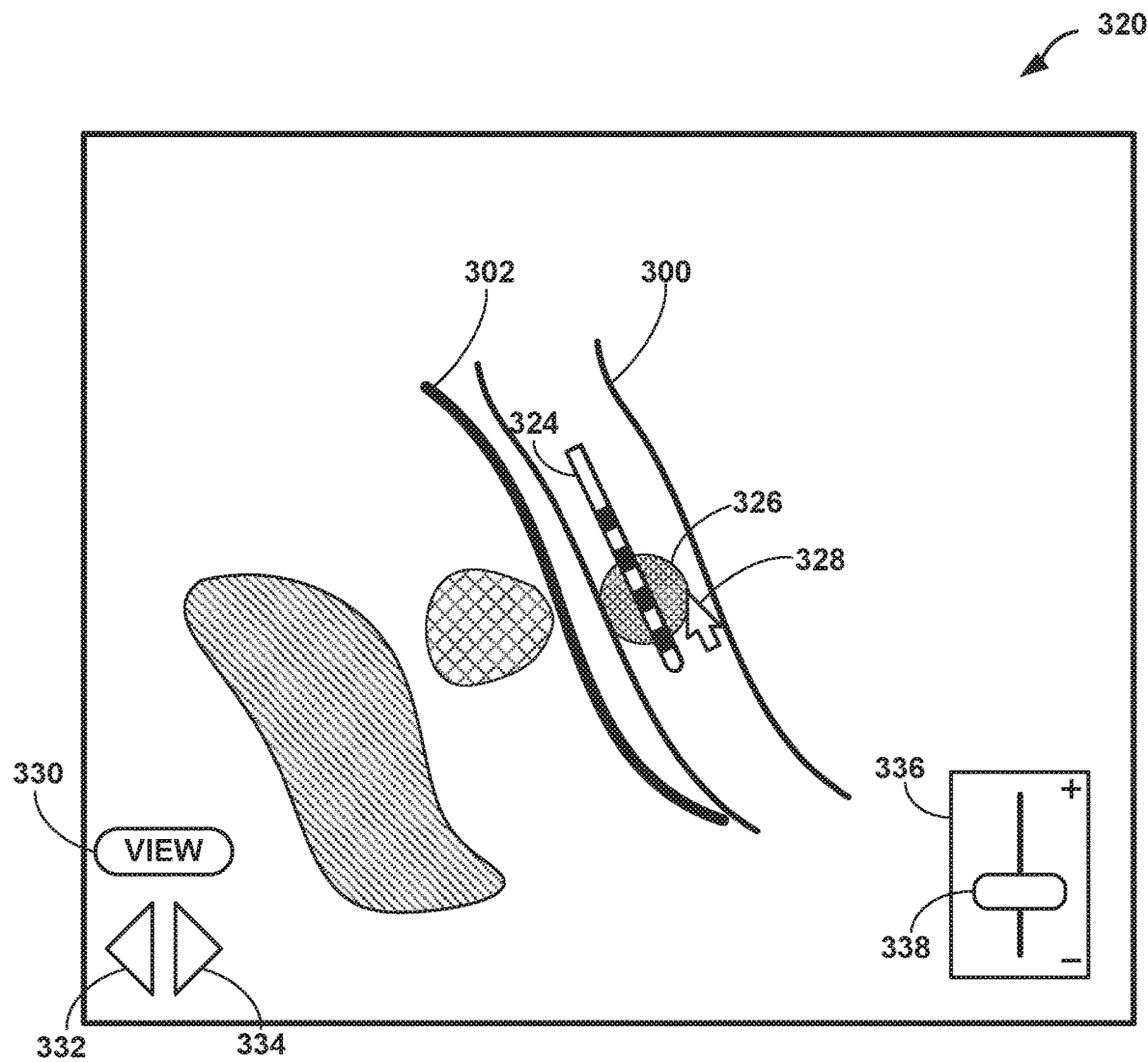
FIG. 20 is a schematic illustration of another example of a GUI that may be presented on the display of the programmer of FIG. 14.

FIG. 20 is a schematic illustration of another example of a GUI 320 that may be presented on the display of programmer 224. A user may interact with GUI 320 via user interface 226 of programmer 224 in order to select desired volumes of influence of denervation therapy. GUI 320 includes a representation of an anatomical region of a patient, for example, a region including target nerve 302. In GUI 320, a device icon 324 representing catheter 102 is displayed within a graphical representation of blood vessel 300.

Differently shaded portions of GUI 320 indicate varying densities of tissue within the region. For example, darker portions may indicate more dense tissue. A user may be able to recognize different anatomical structures or tissue types by viewing GUI 320. It should be noted that GUI 320 shown in FIG. 20 is merely an example image, and actual images may include a wider range of shades and higher image resolution.

GUI 320 further includes pointer 328, previous arrow 332, next arrow 334, fine control input mechanism 336, and control slide 338. Pointer 328 may be controlled with a mouse and buttons, a track-ball, touch-pad, touch screen or other movement input device, which may be a part of user interface 226 of programmer 224. A user may use pointer 328 to drag device icon 324 into position or rotate device icon 324. The user may zoom in to or out of the view for a larger view of anatomical region, or move up, down, left, or right to view a larger or smaller portion of the region.

GUI 320 allows the user to select and adjust a size, and, in some examples, a shape of volume of influence 326, which may be further defined in other orthogonal views. The user may use pointer 328 to drag volume of influence 326 to define a smaller or larger size, which may correspond to a lower or higher RF energy level. For example, the user may click on a border, or perimeter of volume of influence 326, and then drag the border to expand or contract volume of influence 326. This adjustment is the coarse control of the size of volume of influence 326. The user may use pointer 328 to move control slide 338 up to slightly increase the size of volume of influence 326 or down to slightly decrease the size of volume of influence 326.

Processor 225 of programmer 224 may limit the rate of movement of volume of influence 326. For example, processor 225 may limit the movement of volume of influence 326 within GUI 320 to a certain number of steps per second. This rate movement limit may prevent unnecessary calculations in real-time changing of denervation therapy parameter values parameters with modifications of volume of influence 326.

View button 330 may permit a user to switch to another view of the region. The other views may include, for example, a view from a different orientation, or a view based on a different imaging technique.

Figure 21:
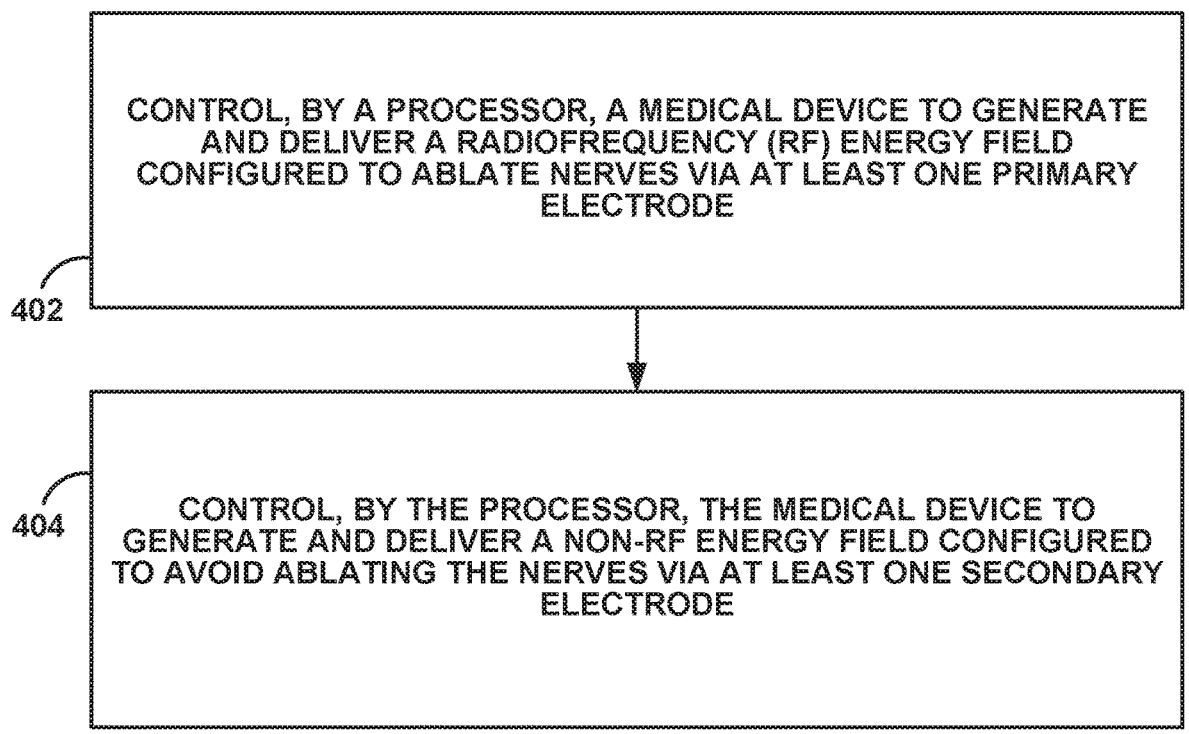
FIG. 21 is a flow diagram illustrating an example technique including delivering a radiofrequency (RF) energy field and delivering a non-RF energy field.

FIG. 21 is a flow diagram illustrating an example technique including delivering a radiofrequency (RF) energy field and delivering a non-RF energy field. While the example technique of FIG. 21 is described with reference to system 100 of FIG. 1 and system 200 of FIG. 14, the example technique of FIG. 21 may be implemented using any suitable system.

The example technique of FIG. 21 includes controlling, by processor 225 of programmer 224, a medical device (for example, generator 214) to generate and deliver a radiofrequency (RF) energy field via at least one primary electrode of plurality of primary electrodes 124 of an electrode array positioned on an elongated member of catheter 102 (402). The RF energy field is configured to ablate nerves at or adjacent a target tissue site. The electrode array includes plurality of primary electrodes 124 spaced apart along the elongated member, and a plurality of secondary electrodes 125 spaced apart along the elongated member. The example technique includes controlling, by processor 225, the medical device to generate and deliver a non-RF energy field via at least one secondary electrode of plurality of secondary electrodes 125 substantially simultaneously with the RF energy field (404). The non-RF energy field is configured to avoid ablating the nerves at or adjacent the target tissue site. In some examples, the non-RF energy field substantially inhibits the RF energy field from extending beyond the non-RF energy field. In some examples, the non-RF energy field is configured to guide the RF energy field to the nerves at or adjacent the target tissue site.

Figure 22:
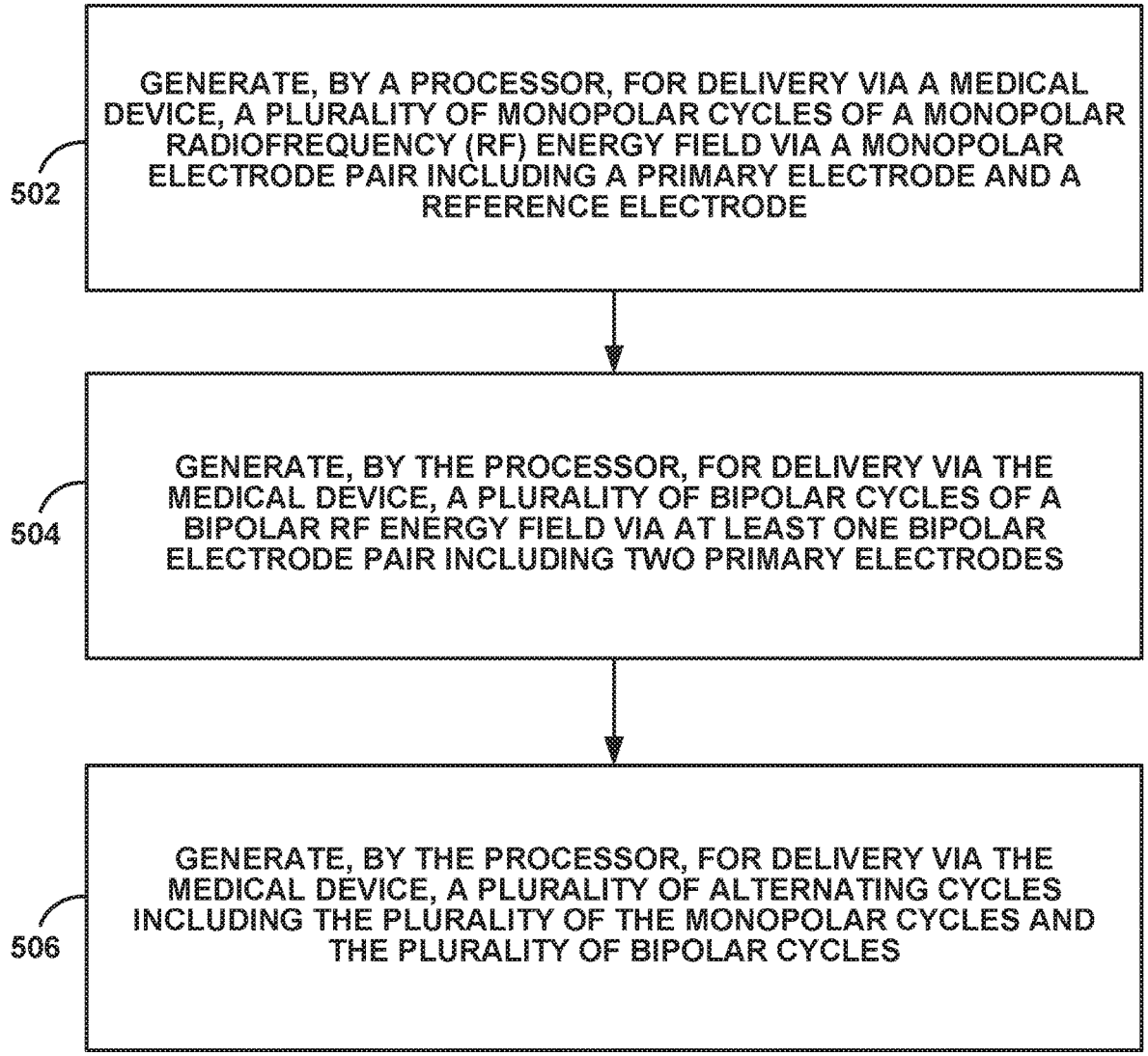
FIG. 22 is a flow diagram illustrating an example technique including delivering alternating cycles of monopolar and bipolar stimulation.

FIG. 22 is a flow diagram illustrating an example technique including delivering alternating cycles of monopolar and bipolar stimulation. While the example technique of FIG. 22 is described with reference to system 100 of FIG. 1 and system 200 of FIG. 14, the example technique of FIG. 22 may be implemented using any suitable system.

In some examples, the example technique of FIG. 22 includes, generating, by processor 225, for delivery via a medical device (for example, generator 214), a plurality of monopolar cycles of a monopolar radiofrequency (RF) energy field via a monopolar electrode pair including a primary electrode of plurality of primary electrodes 124 and a reference electrode (502). The monopolar RF energy field has a first volume of influence at or adjacent a target tissue site. The medical device is electrically coupled to plurality of primary electrodes 124 spaced apart along an elongated member and to the reference electrode. In some examples, the technique of FIG. 22 includes generating, by processor 225, for delivery via the medical device, a plurality of bipolar cycles of a bipolar RF energy field via at least one bipolar electrode pair including two primary electrodes of plurality of primary electrodes 125 (504). The bipolar RF energy field has a second volume of influence smaller than the first volume of influence at or adjacent the target tissue site. The technique of FIG. 22 includes generating, by processor 225, for delivery via the medical device, a plurality of alternating cycles including the plurality of the monopolar cycles and the plurality of bipolar cycles (506). In some examples, the number of the plurality of the bipolar cycles is less than 50% of the number of the plurality of monopolar cycles. In some examples, the number of the plurality of the bipolar cycles is less than 10% of the number of the plurality of monopolar cycles.

Certain aspects of the present technology may take the form of computer-executable instructions, including routines executed by a controller or other data processor. In some embodiments, a controller or other data processor is specifically programmed, configured, and/or constructed to perform one or more of these computer-executable instructions. Furthermore, some aspects of the present technology may take the form of data (e.g., non-transitory data) stored or distributed on computer-readable media, including magnetic or optically readable and/or removable computer discs as well as media distributed electronically over networks. Accordingly, data structures and transmissions of data particular to aspects of the present technology are encompassed within the scope of the present technology. The present technology also encompasses methods of both programming computer-readable media to perform particular steps and executing the steps.

The techniques described in this disclosure may be implemented, at least in part, in hardware, software, firmware, or any combination thereof. For example, various aspects of the described techniques may be implemented within processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various techniques described in this disclosure. In addition, any of the described instructions, units, modules or components may be implemented together or separately as discrete but interoperable logic devices. Depiction of different features as modules or units is intended to highlight different functional aspects and does not necessarily imply that such modules or units must be realized by separate hardware, firmware, or software components. Rather, functionality associated with one or more modules or units may be performed by separate hardware, firmware, or software components, or integrated within common or separate hardware, firmware, or software components.

The techniques described in this disclosure may also be embodied or encoded in a computer system-readable medium, such as a computer system-readable storage medium, containing instructions. Instructions embedded or encoded in a computer system-readable medium, including a computer system-readable storage medium, may cause one or more programmable processors, or other processors, to implement one or more of the techniques described herein, such as when instructions included or encoded in the computer system-readable medium are executed by the processing circuitry. Computer system readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer system readable media. In some examples, an article of manufacture may comprise one or more computer system-readable storage media, for example, non-transitory computer system-readable storage media.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "about" or "approximately," when preceding a value, should be interpreted to mean plus or minus 10% of the value, unless otherwise indicated. Additionally, the term "comprising" is used throughout to mean including at least the recited feature(s) such that any greater number of the same feature and/or additional types of other features are not precluded. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

What is claimed is:

1. A system comprising:
a catheter comprising an elongated member configured to be navigated through a vasculature of a patient, wherein the elongated member comprises an electrode array, the electrode array including:
a plurality of primary electrodes spaced apart along the elongated member, and
a plurality of secondary electrodes spaced apart along the elongated member; and
a console configured to be electrically coupled to the plurality of primary electrodes and the plurality of secondary electrodes, wherein the console is configured to:
generate and deliver a radiofrequency (RF) electric field via at least one primary electrode of the plurality of primary electrodes, wherein the RF electric field is configured to ablate nerves at or adjacent a target tissue site, and
generate and deliver a non-ablative electric field via at least one secondary electrode of the plurality of secondary electrodes substantially simultaneously with the RF electric field to at least partially reduce transmission of the RF electric field, wherein the non-ablative electric field is configured to avoid ablating the nerves at or adjacent the target tissue site.

2. The system of claim 1, wherein the console is configured to control the generation and delivery of the non-ablative electric field via the at least one secondary electrode to partially prevent the RF electric field from extending beyond the non-ablative electric field.

3. The system of claim 1, wherein the console is configured to control the generation and delivery of the non-ablative electric field via the at least one secondary electrode to guide the RF electric field to the nerves at or adjacent the target tissue site by at least preventing transmission of the RF electric field beyond the non-ablative electric field.

4. The system of claim 1, wherein the plurality of primary electrodes includes a coupled electrode pair including a first primary electrode and a second primary electrode proximate one another, and wherein the RF electric field includes a bipolar RF electric field delivered via the first primary electrode and the second primary electrode of the coupled electrode pair.

5. The system of claim 4, wherein the coupled electrode pair is a first coupled electrode pair, and wherein the plurality of primary electrodes includes a third primary electrode and a fourth primary electrode, wherein the plurality of primary electrodes includes a second coupled electrode pair including the second primary electrode and the third primary electrode, wherein the plurality of primary electrodes includes a third coupled electrode pair including the third primary electrode and the fourth primary electrode, wherein the bipolar RF electric field is a first bipolar RF electric field, and wherein the console is configured to generate and deliver the first bipolar RF electric field via the first coupled electrode pair, a second bipolar RF electric field via the second coupled electrode pair, and a third bipolar RF electric field via the third coupled electrode pair.

6. The system of claim 4, wherein the plurality of secondary electrodes includes a first secondary electrode and a second secondary electrode spaced apart from the first secondary electrode, wherein the first primary electrode is positioned on the elongated member between the first and second secondary electrodes, wherein the non-ablative electric field includes a first non-ablative electric field, and wherein the console is configured to:
generate and deliver the first non-ablative electric field via the first secondary electrode;
generate and deliver a second non-ablative electric field via the second secondary electrode; and
control the generation and delivery of one or both of the first or the second non-ablative electric fields to partially prevent the bipolar RF electric field from extending beyond the first or second non-ablative electric fields.

7. The system of claim 1, wherein at least one of the plurality of secondary electrodes differs in at least one electrode characteristic from at least one of the plurality of primary electrodes.

8. The system of claim 1, wherein the elongated member further comprises a plurality of thermal elements spaced apart from one another, wherein the console is configured to deliver, via the plurality of thermal elements, non-ablative thermal energy, at or below about 45° C., to a target tissue site or areas adjacent the target tissue site.

9. The system of claim 1, wherein tissue adjacent the target tissue site includes injected electrically conductive material or injected electrically insulative material, and wherein the injected electrically conductive material or injected electrically insulative material causes a substantially uniform local impedance field at or adjacent the target tissue site.

10. The system of claim 1, wherein to at least partially reduce transmission of the RF electric field, the console is configured to generate and deliver the non-ablative electric field via the at least one secondary electrode to change at least one of a size, a shape, or a directionality of the RF electric field.

11. A method comprising:
controlling, by a processor, a medical device to generate and deliver a radiofrequency (RF) electric field via at least one primary electrode of a plurality of primary electrodes of an electrode array positioned on an elongated member of a catheter, wherein the RF electric field is configured to ablate nerves at or adjacent a target tissue site, wherein the electrode array includes:
the plurality of primary electrodes spaced apart along the elongated member, and
a plurality of secondary electrodes spaced apart along the elongated member; and
controlling, by the processor, the medical device to generate and deliver a non-ablative electric field via at least one secondary electrode of the plurality of secondary electrodes substantially simultaneously with the RF electric field to at least partially reduce transmission of the RF electric field, wherein the non-ablative electric field is configured to avoid ablating the nerves at or adjacent the target tissue site.

12. The method of claim 11, wherein controlling the medical device to generate and deliver the non-ablative electric field includes controlling the generation and delivery of the non-ablative electric field via the at least one secondary electrode to prevent the RF electric field from extending beyond the non-ablative electric field.

13. The method of claim 11, wherein controlling the medical device to generate and deliver the non-ablative electric field includes controlling the generation and delivery of the non-ablative electric field via the at least one secondary electrode to guide the RF electric field to the nerves at or adjacent the target tissue site by at least preventing transmission of the RF electric field beyond the non-ablative electric field.

14. The method of claim 11, wherein the plurality of primary electrodes includes a coupled electrode pair including a first primary electrode and a second primary electrode proximate one another, and wherein the RF electric field includes a bipolar RF electric field delivered via the first primary electrode and the second primary electrode of the coupled electrode pair.

15. The method of claim 14, wherein the coupled electrode pair is a first coupled electrode pair, and wherein the plurality of primary electrodes includes a third primary electrode and a fourth primary electrode, wherein the plurality of primary electrodes includes a second coupled electrode pair including the second primary electrode and the third primary electrode, wherein the plurality of primary electrodes includes a third coupled electrode pair including the third primary electrode and the fourth primary electrode, wherein the bipolar RF electric field is a first bipolar RF electric field, and wherein the method comprises:
controlling, by the processor, the medical device to deliver the first bipolar RF electric field via the first coupled electrode pair;
controlling, by the processor, the medical device to deliver a second bipolar RF electric field via the second coupled electrode pair; and
controlling, by the processor, the medical device to deliver a third bipolar RF electric field via the third coupled electrode pair.

16. The method of claim 14, wherein the plurality of secondary electrodes includes a first secondary electrode and a second secondary electrode spaced apart from the first secondary electrode, wherein the first primary electrode is positioned on the elongated member between the first and second secondary electrodes, and wherein the method comprises:
controlling, by the processor, the medical device to generate and deliver a first non-ablative electric field via the first secondary electrode; and
controlling, by the processor, the medical device to generate and deliver a second non-ablative electric field via the second secondary electrode, wherein the generation and the delivery of the first non-ablative electric field or the second non-ablative electric field are controlled to prevent the bipolar RF electric field from extending beyond the first or second non-ablative electric fields.

17. The method of claim 11, wherein the elongated member further comprises a plurality of thermal elements spaced apart from one another, and wherein the method further comprises, controlling, by the processor, the medical device to deliver, via the thermal elements, non-ablative thermal energy, at or below about 45° C., to a target tissue site or areas adjacent the target tissue site.

18. The method of claim 11, wherein tissue adjacent the target tissue site includes injected electrically conductive material or injected electrically insulative material, and wherein the injected electrically conductive material or injected electrically insulative material causes a substantially uniform local impedance field at or adjacent the target tissue site.

19. A system comprising:
a plurality of primary electrodes;
a plurality of secondary electrodes; and
a console configured to be coupled to the plurality of primary electrodes and the plurality of secondary electrodes and configured to:
generate and deliver a radiofrequency (RF) electric field via a primary electrode of the plurality of primary electrodes, wherein the RF electric field is configured to ablate nerves at or adjacent a target tissue site; and
generate and deliver a non-ablative electric field substantially simultaneously with the RF electric field via a secondary electrode of the plurality of secondary electrodes to change at least one of a size, a shape, or a directionality of the RF electric field, wherein the non-ablative electric field is configured to avoid ablating the nerves at or adjacent the target tissue site.

20. The system of claim 19, wherein the console is configured to control the generation and delivery of the non-ablative electric field substantially via the secondary electrode to prevent the RF electric field from extending beyond the non-ablative electric field.

21. The system of claim 19, wherein the console is configured to control the generation and delivery of the non-ablative electric field via the secondary electrode to guide the RF electric field to the nerves at or adjacent the target tissue site by at least preventing transmission of the RF electric field beyond the non-ablative electric field.

22. The method of claim 11, wherein controlling the medical device to generate and deliver the non-ablative electric field to at least partially reduce transmission of the RF electric field includes controlling the medical device to generate and deliver the non-ablative electric field via the at least one secondary electrode to change at least one of a size, a shape, or a directionality of the RF electric field.

* * * * *